(12) United States Patent
Wozney et al.

(10) Patent No.: US 6,610,513 B2
(45) Date of Patent: Aug. 26, 2003

(54) RECEPTOR PROTEINS

(75) Inventors: John M. Wozney, Hudson, MA (US); Anthony J. Celeste, Hudson, MA (US); R. Scott Thies, Andover, MA (US); Noboru Yamaji, Tsukuba (JP)

(73) Assignee: Genetics Institute, LLC., Cambridge, MA (US)

( * ) Notice: Subject to any disclaimer, the term of this patent is extended or adjusted under 35 U.S.C. 154(b) by 0 days.

(21) Appl. No.: 09/874,628

(22) Filed: Jun. 5, 2001

(65) Prior Publication Data

US 2002/0137133 A1 Sep. 26, 2002

Related U.S. Application Data

(63) Continuation of application No. 08/123,934, filed on Sep. 17, 1993, now Pat. No. 6,291,206.

(51) Int. Cl.[7] .......................... C12P 21/06; C12N 15/74; C12N 5/02; C07H 21/04; C07K 14/00
(52) U.S. Cl. .................. 435/69.1; 435/320.1; 435/325; 536/23.2; 536/235; 530/350
(58) Field of Search .............................. 435/69.1, 320.1, 435/325; 536/23.5, 23.2; 530/350

(56) References Cited

U.S. PATENT DOCUMENTS

| | | | |
|---|---|---|---|
| 5,216,126 A | 6/1993 | Cox et al. | 530/350 |
| 5,217,867 A | 6/1993 | Evans et al. | 435/7.1 |
| 5,218,090 A | 6/1993 | Connors | 530/350 |
| 5,229,495 A | 7/1993 | Ichijo et al. | 530/350 |
| 5,286,654 A | 2/1994 | Cox et al. | 436/501 |
| 5,538,892 A * | 7/1996 | Donahoe et al. | |
| 5,547,854 A * | 8/1996 | Donahoe et al. | |

FOREIGN PATENT DOCUMENTS

| | | |
|---|---|---|
| EP | 0 416 578 A2 A3 | 3/1991 |
| WO | WO 88/00205 | 1/1988 |
| WO | WO 91/18047 | 11/1991 |
| WO | WO 92/20793 | 11/1992 |
| WO | WO 92/22319 | 12/1992 |
| WO | WO 93/09228 | 5/1993 |
| WO | WO 93/19177 * | 9/1993 |
| WO | WO 94/11502 | 5/1994 |

OTHER PUBLICATIONS

Cunningham et al., *Proc. Natl. Acad. Sci. USA* 89: 11740–11744 (1992).
He et al., *Developmental Dynamics* 196: 133–142 (1993).
Wang et al., *Cell* 67: 797–805 (1991).
Nakamura et al., *J. Biol. Chem.* 267: 18924–18928 (1992).
Ebner, *Science* 260: 1344–1348 (1993).
Massague, *Cell,* 69: 1067–1070 (1992).
Matsuzaki et al., *J. Biol. Chem.* 268: 12719–12723 (1993).
Lin, *Cell* 68: 775–785 (1992).
Attisano, *Cell* 68: 97–108 (1992).
Mathews et al., *Cell* 65: 973–982 (1991).
Estevez, M. et al., *Nature* 365: 644–49 (1993).
ten Dijke, et al., *J. Biol. Chem.* 269: 16985–88 (1994).
Koenig et al., *Mol. Cell. Biol.* 14: 5961–74 (1994).
ten Dijke et al., *Gen Bank record no.* Z22535 (1993).
Miyazono, K. et al., *Gen Bank record no.* Z23154 (1993).
Suzuki, et al., *Gen Bank record no.* D16250 (1993).
Dewulf, et al., *Endocrinology,* 136: 2652–2663 (1995).

* cited by examiner

*Primary Examiner*—Yvonne Eyler
*Assistant Examiner*—Janet L. Andres
(74) *Attorney, Agent, or Firm*—Finnegan, Henderson, Farabow, Garrett & Dunner, L.L.P.

(57) ABSTRACT

Novel serine/threonine receptor proteins and BMP receptor proteins are disclosed, as well as DNA molecules encoding these proteins and methods of using the receptor proteins. Further disclosed are truncated BMP receptor proteins and molecules which act as ligands to these BMP receptor proteins.

4 Claims, No Drawings

RECEPTOR PROTEINS

This is a continuation of application Ser. No. filed on Sep. 17, 1993 now U.S. Pat. No. 6,291,206 the entire disclosure of which is hereby incorporated by reference.

FIELD OF THE INVENTION

The present invention relates to novel serine/threonine kinase receptor proteins, including a novel family of receptor proteins to bone morphogenetic proteins (BMPs). More particularly, the present invention relates to receptor proteins which are able to bind to BMPs, including BMP-2 and BMP-4. The present invention further relates to methods of isolating novel BMP receptor proteins using newly identified DNA fragments as probes for isolating such proteins.

BACKGROUND OF THE INVENTION

Bone morphogenetic proteins (BMPs) are a family of proteins which have been identified as having the ability to induce the formation of bone and cartilage in tissue extracts. BMPs are a subfamily within the TGF-β superfamily. BMPs have multiple therapeutic uses, including a wide variety of settings where bone has been lost through physiological or traumatic processes.

The TGF-β superfamily of proteins have been shown to bind to serine/threonine kinase receptors. Massague, *Cell,* 69:1067–1070 (1992); Attisano et al., *Cell* 68:97–108 (1992); Lin et al., *Cell,* 68:775–785 (1992); Wang et al., *Cell* 67:797–805 (1991). Similarly, activin receptors have been isolated and characterized as a predicted transmembrane serine kinase. Mathews et al., *Cell* 65:973–982 (1991); Nakamura et al., *J. Biol. Chem.* 267:18924–18928 (1992): Ebner et al., *Science,* 260:1344–1348 (1993) describe the existence of Type I and Type II TGF-β receptors, and the effects of the Type I receptor on binding of TGF-β to the Type II receptor.

Type I receptor proteins have been reported not to bind to their ligand molecules independently, but, acting in concert with Type II receptor proteins, are observed to contribute to increased binding to the ligand. See Matsuzaki et al., *J. Biol. Chem.,* 268:12719–12723 (1993); Ebner et al., *Science,* 260:1344–1348 (1993).

Paralkar et al., *PNAS USA* 88:3397–3401 (1991) describes the presence of high affinity binding sites for BMP-4 on MC3T3E1 and NIH3T3 cells. No competition by TGF-β was found for the BMP-4 binding proteins, nor was competition by BMP-4 for TGF-β receptors observed in Attisano et al., *Cell* 68:97–108 (1992).

SUMMARY OF THE INVENTION

In one embodiment, the present invention comprises a purified and isolated DNA molecule which encodes a BMP receptor protein, said DNA molecule preferably comprising the clones CFK1-43a and CFK1-23a, or a DNA sequence selected from the group consisting of SEQ ID NO:1 and SEQ ID NO:3.

The present invention further comprises purified and isolated DNA molecules which encode BMP receptor proteins, said BMP receptor proteins preferably comprising an amino acid sequence selected from the group consisting of SEQ ID NO:2 and SEQ ID NO:4. In another embodiment, the present invention comprises a BMP receptor protein CFK1-43a and CFK1-23a, comprising an amino acid sequence selected from the group consisting of SEQ ID NO:2 and SEQ ID NO:4.

The present invention further comprises DNA molecules comprising a DNA sequence selected from the group consisting of SEQ ID NO:5, SEQ ID NO:7 and SEQ ID NO:9, and DNA molecules which encode serine/threonine kinase receptor proteins comprising an amino acid sequence selected from the group consisting of SEQ ID NO:6, SEQ ID NO:8 and SEQ ID NO:10. These DNA molecules and proteins are related to the BMP family of receptors. Among other uses, these DNA molecules are presently useful as probes for isolating and purifying additional novel BMP receptors.

The present invention also comprises novel DNA sequences which encode receptor proteins, which novel DNA sequences are identified by a method using DNA sequence encoding all or a fragment of the receptor proteins of the present invention. In preferred embodiments, the novel DNA sequences are identified using DNA sequence from the serine/threonine kinase domain of a receptor, which is highly conserved among the family of BMP receptors. Alternatively, DNA sequence encoding the ligand binding domain could be used to identify additional novel BMP receptor encoding sequences.

The present invention further comprises DNA molecules encoding soluble, truncated receptor proteins, and the soluble proteins themselves. The truncated receptor proteins preferably comprise the ligand binding domain, but not the serine/threonine kinase and transmembrane domains, of the receptor protein. The truncated receptor proteins are soluble, and will be secreted into supernatant by mammalian cells. Thus, when expressed in mammalian cells using a DNA molecule encoding a truncated receptor protein, the truncated receptor protein will be secreted rather than expressed on the surface of the host cell. The truncated receptor protein thereby expressed still binds specifically to BMPs, and can be used to block receptors from mediating the cellular processes in which they normally participate in as signalling mechanisms by competition for the same ligand. The truncated receptor protein could compete with receptor proteins normally expressed on the surface of responsive cells for functional ligand and inhibit the formation of a functional receptor-ligand complex, thereby blocking the normal signalling mechanism of the complex and the cellular processes normally affected by functional receptor-ligand interactions.

In one aspect, the invention provides a method for producing cells expressing more than one receptor protein comprising culturing a selected host cell containing a polynucleotide sequence encoding a first selected receptor protein, truncated receptor protein, or active fragment thereof and a polynucleotide sequence encoding a second selected receptor protein, truncated receptor protein, or active fragment thereof. The resulting cells, which will express multiple co-expressed, biologically active receptors, may be isolated and used in a therapeutic composition.

Another aspect of the current invention comprises ligands for the BMP receptors and truncated BMP receptor protein, said ligands being characterized by the ability to bind to the receptors. Such ligands may stimulate growth of bone and/or cartilage, or may be involved in influencing other developmental processes. Said ligands may be monoclonal antibodies, small peptide BMP analogues, or small organic molecule BMP analogues as further characterized herein. In a preferred embodiment, said ligands comprise antibodies against the truncated, soluble receptor protein and the receptor proteins of the invention. These antibodies can be employed in a variety of diagnostic and therapeutic applications. Such antibodies can be used to identify cell types which naturally express receptors of the invention and may therefore have the capacity to elicit a biological response upon exposure to the appropriate ligand. These antibodies can be further useful in the identification of additional receptor proteins capable of binding to other individual BMPs and/or BMP heterodimers. Additionally such antibodies are useful in blocking the formation of functional receptor-ligand complexes and thus inhibit the cellular responses that would normally be mediated by these complexes. Alternatively, such antibodies may mimic the effect of BMP by interacting with the receptor in a way that would stimulate the cellular responses that would normally be mediated by a functional receptor-ligand complex.

In yet another embodiment, the invention comprises pharmaceutical compositions comprising a compound first identified for such use as a ligand for the truncated BMP receptor and therapeutic methods for the treatment of bone and/or cartilage disorders comprising administering a ligand for the truncated BMP receptor.

Other aspects and advantages of the present invention will be apparent upon consideration of the following detailed description and preferred embodiments thereof.

BRIEF DESCRIPTION OF THE SEQUENCES

SEQ ID NO:1 comprises DNA and amino acid sequence of the BMP receptor protein CFK1-23a, isolated from rat cell line CFK1. This DNA contained in plasmid CFK1-23a, which has been deposited and accorded ATCC #69378, further described below.

SEQ ID NO:2 comprises the amino acid sequence encoded by the CFK1-23a DNA sequence.

SEQ ID NO:3 comprises DNA and amino acid sequence of the BMP receptor protein CFK1-43a, isolated from rat cell line CFK1. This DNA contained in plasmid CFK1-43a has been deposited and accorded ATCC #69381, further described below.

SEQ ID NO:4 comprises the amino acid sequence encoded by the CFK1-43a DNA sequence.

SEQ ID NO:5 comprises DNA and amino acid sequence of the serine/threonine kinase receptor protein CFK1-10a, isolated from rat cell line CFK1. This DNA contained within plasmid CFK1-10a has been deposited and accorded ATCC #69380, further described below.

SEQ ID NO:6 comprises the amino acid sequence encoded by the CFK1-10a DNA sequence.

SEQ ID NO:7 comprises DNA and amino acid sequence of the serine/kinase receptor protein W101, isolated from murine cell line W-20-17. This DNA contained in plasmid pMT101 has been deposited and accorded ATCC #69379, further described below.

SEQ ID NO:8 comprises the amino acid sequence encoded by the W101 DNA sequence.

SEQ ID NO:9 comprises DNA and amino acid sequence of the serine/kinase receptor protein W120, isolated from murine cell line W-20-17. This DNA contained in plasmid pMT120E has been deposited and accorded ATCC #69377, further described below.

SEQ ID NO:10 comprises the amino acid sequence encoded by the W120 DNA sequence.

SEQ ID NO:11 comprises DNA and amino acid sequence of the serine/kinase receptor protein KDA-B5. This DNA was used as a probe to identify novel serine/kinase receptors of the present invention.

SEQ ID NO:12 comprises the amino acid sequence encoded by the KDA-B5 DNA sequence.

SEQ ID NO:13: comprises the DNA sequence of oligonucleotide primer A.

SEQ ID NO:14: comprises the DNA sequence of oligonucleotide primer B.

SEQ ID NO:15: comprises the DNA sequence of oligonucleotide primer C.

SEQ ID NO:16 comprises the DNA sequence of oligonucleotide primer D.

SEQ ID NO:17 comprises the DNA sequence of oligonucleotide primer E.

SEQ ID NO:18: comprises the amino acid sequence of a portion of KDA-B5 used to design oligonucleotide primer A.

SEQ ID NO:19 comprises the amino acid sequence of a portion of KDA-B5 used to design oligonucleotide primer B through E.

DETAILED DESCRIPTION OF THE INVENTION

Bone morphogenetic proteins are characterized by their ability to promote, stimulate or otherwise induce the formation of cartilage and/or bone. The ability of these proteins to demonstrate cartilage and/or bone formation activity in the rat bone formation assay described below. These proteins can be used in compositions which may be used to induce bone and/or cartilage formation. These BMP compositions may also be used for wound healing and tissue repair. Further uses of such compositions include the treatment of bone and/or cartilage defects, periodontal disease and other tooth repair processes, treatment of osteoporosis and increase of neuronal survival.

The BMP receptors and truncated receptors of the present invention are useful, among other uses, for the identification of BMPs, the identification of further BMP receptors, and the identification of ligands or molecules, including antibodies, which are able to mimic the binding characteristics of BMPs. These ligands may act as agonist or antagonists, depending upon the individual ligand. The activity of the ligands may be characterized in an assay for BMP activity, such as the W-20-17 alkaline phophatase induction assay and rat ectopic bone formation assay, described at Examples XII and XIII below. The BMP receptors are also useful in inhibiting the effects of BMPs, where such inhibition is desired.

BMP receptor proteins of the present invention may be characterized by an amino acid sequence comprising amino acid # 1–532 of SEQ ID NO:2; or amino acid # 1–502 of SEQ ID NO:4.

The purified human BMP receptor proteins of the present invention may be produced by culturing a host cell transformed with a DNA sequence comprising the DNA coding sequence of SEQ ID NO:1 from nucleotide # 61 to nucleotide 1656 (or to 1659 with the stop codon); or SEQ ID NO:3 from nucleotide #247 to nucleotide 1752 (or to 1755 stop codon); and recovering and purifying from the transformed cell membrane a protein which contains the derived amino acid sequence, or a substantially homologous sequence as represented by amino acid # 24 to # 532 of SEQ ID NO:2; or amino acid # 8 to # 502 of SEQ ID NO:4. Since the BMP receptor proteins expressed in this manner are expected to remain associated with the cell membrane of the transformed cell, recombinant receptor proteins of the invention can be dissociated from the transformed cell membrane and are then purified by isolating them from other proteinaceous materials with which they are co-produced and from other contaminants present.

Truncated BMP receptor proteins of the present invention may be characterized by an amino acid sequence comprising amino acid # 1–149 of SEQ ID NO:2; or amino acid # 1–124 of SEQ ID NO:4.

The purified human truncated BMP receptor proteins of the present invention may be produced by culturing a host cell transformed with a DNA sequence comprising the DNA coding sequence of SEQ ID NO:1 from nucleotide # 61 to nucleotide 507; or SEQ ID NO:3 from nucleotide # 247 to nucleotide 618; and recovering and purifying from the culture medium a protein which contains the derived amino acid sequence, or a substantially homologous sequence, as represented by amino acid # 24 to # 149 of SEQ ID NO:2; or amino acid # 8 to # 124 of SEQ ID NO:4. In the above amino acid sequences, the secretory leader sequence (e.g., amino acids 1 to 23 of SEQ ID NO:2) will not be present since these are typically cleaved away from secreted proteins. The leader sequence predicted for SEQ ID NO:4 by standard computer programs is amino acids 1 to 7; however, it is contemplated that the actual leader sequence may be longer since seven amino acids is unusually short for a leader sequence. Thus, the protein purified from culturing host cells transformed with a DNA molecule comprising the DNA sequence of SEQ ID NO:3 from nucleotide # 247 to nucleotide 618 may be shorter than amino acid # 8 to # 124 of SEQ ID NO:4.

The truncated BMP receptor proteins recovered from the culture medium are purified by isolating them from other proteinaceous materials with which they are co-produced and from other contaminants present.

Other serine/threonine kinase receptor proteins of the present invention may be characterized by an amino acid sequence comprising amino acid # 1–509 of SEQ ID NO:6.

The purified serine/threonine kinase receptor proteins of the present invention may be produced by culturing a host cell transformed with a DNA sequence comprising the DNA coding sequence of SEQ ID NO:5 from nucleotide # 474 to nucleotide 2000 (or to 2003 stop codon); and recovering and purifying from the transformed cell membrane a protein which contains the derived amino acid sequence, or a substantially homologous sequence as represented by amino acid # 18 to # 509 of SEQ ID NO:6. Since the serine/threonine kinase receptor proteins expressed in this manner are expected to remain associated with the cell membrane of the transformed cell, recombinant receptor proteins of the invention can be dissociated from the transformed cell membrane and are then purified by isolating them from other proteinaceous materials with which they are co-produced and from other contaminants present.

Truncated serine/threonine kinase receptor proteins of the present invention may be characterized by an amino acid sequence comprising amino acid # 1–121 of SEQ ID NO:6.

The purified human truncated serine/threonine kinase receptor proteins of the present invention may be produced by culturing a host cell transformed with a DNA sequence comprising the DNA coding sequence of SEQ ID NO:5 from nucleotide # 474 to nucleotide 836 and recovering and purifying from the culture medium a protein which contains the derived amino acid sequence, or a substantially homologous sequence as represented by amino acid # 18 to # 121 of SEQ ID NO:6. The truncated serine/threonine kinase receptor proteins recovered from the culture medium are purified by isolating them from other proteinaceous materials with which they are co-produced and from other contaminants present.

Serine/kinase receptor proteins of the present invention may be characterized by an amino acid sequence comprising amino acid # 1–505 of SEQ ID NO:8; or amino acid # 1–503 of SEQ ID NO:10.

The purified serine/kinase receptor proteins of the present invention may be produced by culturing a host cell transformed with a DNA sequence comprising the DNA coding sequence of SEQ ID NO:7 from nucleotide # 80 to nucleotide 1594 (or to 1597 stop codon); or SEQ ID NO:9 from nucleotide # 83 to nucleotide 1591 (or to 1594 stop codon); and recovering and purifying from the transformed cell membrane a protein which contains the derived amino acid sequence, or a substantially homologous sequence as represented by amino acid # 24 to # 505 of SEQ ID NO:8; or amino acid # 30 to # 503 of SEQ ID NO:10. Since the serine/kinase receptor proteins expressed in this manner are expected to remain associated with the cell membrane of the transformed cell, recombinant receptor proteins of the invention can be dissociated from the trans formed cell membrane and are then purified by isolating them from other proteinaceous materials with which they are co-produced and from other contaminants present.

Truncated serine/threonine kinase receptor proteins of the present invention may be characterized by an amino acid sequence comprising amino acid # 1–122 of SEQ ID NO:8; or amino acid # 1–121 of SEQ ID NO:10.

The purified human truncated serine/threonine kinase receptor proteins of the present invention may be produced by culturing a host cell transformed with a DNA sequence comprising the DNA coding sequence of SEQ ID NO:7 from nucleotide # 80 to nucleotide 445; or SEQ ID NO:9 from nucleotide # 83 to nucleotide 445; and recovering and purifying from the culture medium a protein which contains the derived amino acid sequence, or a substantially homologous sequence, as represented by amino acid # 24 to # 122 of SEQ ID NO:8; or amino acid # 30 to # 121 of SEQ ID NO:10. The truncated serine/threonine kinase receptor proteins recovered from the culture medium are purified by isolating them from other proteinaceous materials with which they are co-produced and from other contaminants present.

The present invention also encompasses DNA molecules comprising the novel DNA sequences, free of association with DNA sequences encoding other proteinaceous materials, and coding for the expression of the above receptor proteins. These DNA sequences include those depicted in SEQ ID NOS:1, 3, 5, 7 and 9, in a 5' to 3' direction and those sequences which hybridize under stringent hybridization conditions [see, T. Maniatis et al, *Molecular Cloning* (*A Laboratory Manual*), Cold Spring Harbor Laboratory (1982), pages 387 to 389] to the DNA sequences of SEQ ID NOS:1, 3, 5, 7 and 9; and encode a protein having the ability to bind to BMP or which is useful to isolate novel BMP receptors.

Similarly, DNA sequences which code for the above receptor polypeptides coded for by the amino acid sequences of SEQ ID NO:2, 4, 6, 8 and 10, but which differ in codon sequence due to the degeneracies of the genetic code or allelic variations (naturally-occurring base changes in the species population which may or may not result in an amino acid change) also encode the novel receptor proteins described herein. Variations in the DNA sequences of SEQ ID NOS:1, 3, 5, 7 and 9 which are caused by point mutations or by induced modifications (including insertion, deletion, and substitution) to enhance the activity, half-life or production of the polypeptides encoded thereby are also encompassed in the invention.

Another aspect of the present invention provides a novel method for producing receptor proteins. The method of the present invention involves culturing a suitable cell line, which has been transformed with a DNA molecule comprising a DNA sequence coding on expression for a receptor protein, under the control of known regulatory sequences. The transformed host cells are cultured and the receptor proteins recovered and purified from the transformed cell membrane. The purified proteins are substantially free from other proteins with which they are co-produced as well as from other contaminants.

Another aspect of the present invention provides a novel method for producing truncated receptor proteins. The method of the present invention involves culturing a suitable cell line, which has been transformed with a DNA molecule comprising a DNA sequence coding on expression for a truncated receptor protein, under the control of known regulatory sequences. The transformed host cells are cultured and the truncated receptor proteins recovered and purified from the culture medium. The purified proteins are substantially free from other proteins with which they are co-produced as well as from other contaminants.

Suitable cells or cell lines for production of the receptor proteins or truncated receptor proteins may be mammalian cells, such as Chinese hamster ovary cells (CHO) or BHK cells. The selection of suitable mammalian host cells and methods for transformation, culture, amplification, screening and product production and purification are known in the art. See, e.g., Gething and Sambrook, Nature, 293:620–625 (1981), or alternatively, Kaufman et al, Mol. Cell. Biol., 5(7):1750–1759 (1985) or Howley et al, U.S. Pat. No. 4,419,446. Another suitable mammalian cell line, which is described in the accompanying examples, is the monkey COS-1 cell line. The mammalian cell line CV-1 may also be suitable.

Bacterial cells may also be suitable hosts. For example, the various strains of E. coli (e.g., HB101, MC1061) are well-known as host cells in the field of biotechnology. Various strains of B. subtilis, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, Genetic Engineering, 8:277–298 (Plenum Press 1986) and references cited therein.

Another aspect of the present invention provides vectors for use in expression of these novel receptor polypeptides. Preferably, the vectors contain the full novel DNA sequences described above which encode the novel receptor proteins of the invention. Additionally, the vectors contain appropriate expression control sequences permitting expression of the receptor protein sequences.

Alternatively, vectors incorporating modified DNA sequences as described above are also embodiments of the present invention and useful in the production of the receptor proteins. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to one of skill in the art and may be selected depending upon the selected host cells. Such selection is routine and does not form part of the present invention.

The BMP receptor proteins of the present invention, such as CFK1-23a and CFK1-43a, have been found to bind to members of the BMP family, preferably BMP-2 and BMP-4, but not to TGF-$\beta$. Thus, the BMP receptor proteins of the present invention are distinguished from TGF-$\beta$ receptors, which bind to TGF-$\beta$.

The present invention may include co-transfection of cells with DNA molecules comprising DNA sequences encoding multiple receptor proteins in order to achieve binding to a ligand molecule such as a BMP. Thus, for example, a DNA molecule comprising a DNA sequence encoding the receptor protein CFK1-10a may be co-transfected into cells along with a DNA molecule comprising a DNA sequence encoding receptor protein CFK1-23a or CFK1-43a.

The DNA molecules comprising DNA sequences encoding the receptor proteins of the present invention are useful for the production of cells which express receptor proteins. These cells, when transformed with the DNA molecules of the present invention, will express receptor proteins on their surface. In turn, these cells will bind more readily to the ligand and may demonstrate increased responsiveness to the ligand. For example, cells which express the BMP receptor proteins of the present invention exhibit increased binding to BMP-2 and BMP-4, and will exhibit increased responsiveness to BMPs such as BMP-2 and BMP-4. The increased BMP response is desirable for accelerating the effects of BMPs, which include the osteoinductive promotion of bone growth and cartilage regeneration.

The BMP receptor proteins of the present invention are useful for isolating BMP. Additionally, BMP receptor proteins of the invention are useful in the identification of novel molecules related to BMPs which may be capable of inducing the formation of bone or cartilage or may be involved in influencing other developmental processes. In addition, the BMP receptor proteins are useful for identifying and/or quantifying BMP-2 and/or BMP-4 in a sample, as well as for inhibiting the effects of BMP-2 or BMP-4 on cells. The BMP receptors of the present invention may further be useful in identifying synthetic and naturally-occurring chemical entities which are able to mimic the binding effects of BMP-2 and/or BMP-4. The BMP receptor proteins of the invention may also be useful in identifying synthetic and naturally-occurring chemical entities which are able to antagonize and/or inhibit the binding effects of BMP-2 and/or BMP4. The BMP receptor proteins may also be useful in identifying compounds which play a role in regulating the expression of BMP receptor proteins. Those compounds could be used in order to stimulate BMP-responsiveness, for example, bone growth, in particular tissues or cells of interest.

The novel serine/threonine kinase receptor proteins of the present invention also include W101 and W120, which have been isolated from murine cell line W-20-17, a cell line which is known to be responsive to BMP. The DNA encoding one of these novel receptor proteins has been used as a probe in order to isolate other clones which are potentially members of the class of BMP receptor proteins, including the CFK1-23a and CFK1-43a clones, which have been confirmed to encode proteins which are members of the BMP receptor family. Thus, the DNA molecules comprising DNA sequence encoding the serine/kinase receptor proteins of the present invention are useful for the isolation of DNA encoding BMP receptor proteins, and the present invention includes such a method of using the DNA molecules comprising DNA sequence encoding serine/threonine kinase receptor proteins, as well as the novel BMP receptor proteins which are thereby isolated.

In one embodiment of the present invention, novel DNA sequences which encode BMP receptor proteins are identified by a method using DNA sequence encoding all or a fragment of the serine/kinase receptor proteins of the present invention. In preferred embodiments, the novel DNA sequences are identified using DNA sequence encoding the serine/threonine kinase domain of a receptor. Alternatively, DNA sequence encoding the ligand binding domain could be used to identify additional novel BMP receptor encoding sequences.

Thus, the present invention further comprises methods of identifying new BMP receptor proteins and DNA molecules encoding those proteins, and the proteins and DNA molecules thus identified. The method comprises preparing a DNA fragment which encodes a selected domain of a BMP receptor protein, preferably the kinase domain of a BMP receptor protein, or alternatively a DNA fragment encoding the ligand binding domain, and using that fragment as a probe to screen either a genomic or cDNA library. The cDNA library is preferably prepared from a cell line known to express BMP receptors. These include the murine cell line W-20-17 and the rat cell line CFK1. The DNA sequences which are thus identified share homology with the known BMP receptor protein, and thus are expected to encode a protein which will bind to one or more BMPs. Using methods known in the art, one can clone the entire DNA sequence which is thereby identified and use it to express the newly identified BMP receptor protein. Identification of the new protein as a BMP receptor protein is confirmed using the binding assay described in Example VI.

Another embodiment of the present invention comprises DNA molecules comprising DNA sequences encoding truncated receptor proteins, and the truncated proteins themselves. The truncated receptor proteins preferably comprise the ligand binding domain, but not the serine/threonine kinase and transmembrane domains, of the receptor protein. The truncated receptor proteins are soluble, and will be secreted into supernatant by mammalian cells. Thus, when expressed in mammalian cells using a DNA molecule encoding a truncated receptor protein, the truncated receptor protein will be secreted rather than expressed on the surface of the host cell. The truncated receptor protein thereby expressed still binds specifically to its ligand. Thus, the truncated BMP receptor proteins can be used to block BMP receptors of the invention from mediating the cellular processes in which they normally participate in as signalling mechanisms. The truncated receptor protein could compete with receptor proteins normally expressed on the surface of responsive cells for functional ligand and inhibit the formation of a functional receptor-ligand complex, thereby blocking the normal signalling mechanism of the complex and the cellular processes normally affected by functional receptor-ligand interactions.

Compositions containing the truncated BMP receptor proteins of the present invention may be used for the inhibition of the effects of BMPs such as BMP-2 and/or BMP-4 on cells. The present invention includes therapeutic methods comprising administering such a composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the desired site. Therapeutically useful agents, such as growth factors (e.g., BMPs, TGF-β, FGF, IGF), cytokines (e.g., interleukins and CSFs) and antibiotics, may also optionally be included in or administered simultaneously or sequentially with, the receptor composition in the methods of the invention.

Another embodiment of the present invention comprises cells which have been transformed with the DNA molecules comprising DNA sequences encoding the BMP receptor proteins of the present invention. These cells will express BMP receptors on their surface, which will increase the cells' responsiveness to BMP. Thus, cells transformed with the DNA molecules encoding the BMP receptor proteins may be administered therapeutically, to promote response to BMP, for example, bone and/or cartilage regeneration at a desired site.

There is a wide range of methods which can be used to deliver the cells expressing BMP receptor proteins to a site for use in promoting a BMP response such as bone and or cartilage regeneration. In one embodiment of the invention, the cells expressing BMP receptor protein can be delivered by direct application, for example, direct injection of a sample of such cells into the site of bone or cartilage damage. In a particular embodiment, these cells can be purified. In a preferred embodiment, the cells expressing BMP receptor protein can be delivered in a medium or matrix which partially impedes their mobility so as to localize the cells to a site of bone or cartilage injury. Such a medium or matrix could be semi-solid, such as a paste or gel, including a gel-like polymer. Alternatively, the medium or matrix could be in the form of a solid, preferably, a porous solid which will allow the migration of cells into the solid matrix, and hold them there while allowing proliferation of the cells.

In a method of the present invention, the cells expressing BMP receptors are applied in the desired site as described above, and BMP is applied. The BMP may be applied simultaneously or immediately following application of the cells expressing BMP receptors. BMPs are known and have been described as follows: BMP-2 (sometimes referred to as BMP-2A) and BMP-4 (sometimes referred to as BMP-2B), U.S. Pat. No. 5,013,649; BMP-3 U.S. Pat. No. 5,116,738; BMP-5, U.S. Pat. No. 5,106,748; BMP-6, U.S. Pat. No. 5,187,076; BMP-7, U.S. Pat. No. 5,141,905; BMP-8, PCT Publication No. WO93/00432; BMP-9, Ser. No. 07/720,690, filed on Jun. 25, 1991; BMP-10, Ser. No. 08/061,695, filed on May 12, 1993. Heterodimers are described in U.S. patent application Ser. No. 07/787,496, filed on Apr. 7, 1992. The disclosure of the above references are hereby incorporated herein by reference as if fully reproduced herein. The BMP may be applied in manners known in the art, such as described in the above patents, as well as in U.S. Pat. No. 5,171,579, the disclosure of which is also hereby incorporated by reference.

Expression of Receptor Protein

In order to produce receptor protein, the DNA encoding the desired protein is transferred into an appropriate expression vector and introduced into mammalian cells or other preferred eukaryotic or prokaryotic hosts by conventional genetic engineering techniques. The presently preferred expression system for biologically active recombinant receptor protein is stably transformed mammalian cells.

One skilled in the art can construct mammalian expression vectors by employing the sequence of SEQ ID NO:1, 3, 5, 7 or 9, or other DNA sequences containing the coding sequences of SEQ ID NO:1, 3, 5, 7 or 9, or other modified sequences and known vectors, such as pCD [Okayama et al., *Mol. Cell Biol,* 2:161–170 (1982)] and pJL3, pJI4 [Gough et al., *EMBO J.,* 4:645–653 (1985)]. The receptor protein cDNA sequences can be modified by removing the non-coding nucleotides adjacent to the 5' and 3' ends of the coding region. The deleted noncoding nucleotides may or may not be replaced by other sequences known to be beneficial for expression. The transformation of these vectors into appropriate host cells can result in expression of receptor proteins.

One skilled in the art can manipulate the sequences of SEQ ID NO:1, 3, 5, 7 or 9 by eliminating or replacing the mammalian regulatory sequences flanking the coding sequence with bacterial sequences to create bacterial vectors for intracellular or extracellular expression by bacterial cells. For example, the coding sequences can be further manipulated (e.g. ligated to other known linkers or modified by deleting non-coding sequences therefrom or altering nucleotides therein by other known techniques). The modified receptor protein coding sequence can then be inserted into a known bacterial vector using procedures such as described in T. Taniguchi et al., *Proc. Natl Acad. Sci. USA*, 77:5230–5233 (1980). This exemplary bacterial vector can then be transformed into bacterial host cells and receptor protein expressed thereby. For a strategy for producing extracellular expression of receptor proteins in bacterial cells., see, e.g. European patent application EPA 177,343.

Similar manipulations can be performed for the construction of an insect vector [See, e.g. procedures described in published European patent application 155,476] for expression in insect cells. A yeast vector can also be constructed employing yeast regulatory sequences for intracellular or extracellular expression of the receptor proteins of the present invention by yeast cells. [See, e.g., procedures described in published PCT application WO86/00639 and European patent application EPA 123,289].

A method for producing high levels of a receptor protein of the invention in mammalian cells involves the construction of cells containing multiple copies of one or more of the heterologous receptor genes. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a BMP receptor protein of the invention in operative association with other plasmid sequences enabling expression thereof and the DHFR expression plasmid pAdA26SV(A)3 [Kaufman and Sharp, *Mol. Cell. Biol.*, 2:1304 (1982)] can be co-introduced into DHFR-deficient CHO cells, DUKX-BII, by calcium phosphate coprecipitation and transfection, electroporation, protoplast fusion or lipofection. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.*, 5:1750 (1983).

Transformants are cloned, and binding to BMP-2 or BMP-4 is measured by the binding assay described above in Example VI. BMP-2 and BMP-4 binding should increase with increasing levels of MIX resistance. Similar procedures can be followed to produce other related BMP receptor proteins.

Co-Expression of Multiple Receptor Proteins

According to one embodiment of this invention, the host cell may be co-transfected with one or more vectors containing coding sequences for one or more receptor proteins, truncated receptor proteins or active fragments thereof. Each receptor polynucleotide sequence may be present on the same vector or on individual vectors co-transfected into the cell. Alternatively, the polynucleotides encoding receptors, truncated receptors or their fragments may be incorporated into a chromosome of the host cell. Additionally, a single transcription unit may encode single copy of two genes encoding different receptor proteins.

According to another embodiment of this invention, the selected host cell containing the two polypeptide encoding sequences is a hybrid cell line obtained by fusing two selected, stable host cells, each host cell transfected with, and capable of stably expressing, a polynucleotide sequence encoding a selected first or second receptor protein, truncated receptor protein or active fragment thereof.

In another aspect of the present invention, therefore, there are provided compositions of cells which express more than one recombinant receptor protein, truncated receptor protein, or active fragments thereof which retain the binding characteristics of the receptor or truncated receptor. Also provided are compositions of truncated truncated receptor proteins secreted by host cells. The cells, proteins, and compositions of receptor proteins, truncated receptor proteins or active fragments thereof may be characterized by their ability to bind selectively to BMPs with greater binding affinity than to other proteins in the TGF-β superfamily in a binding assay.

The cells and compositions may comprise one or more BMP receptor proteins, truncated BMP receptor proteins, or active fragments thereof; or of one or more serine/threonine kinase receptor proteins, truncated serine/threonine kinase receptor proteins, or active fragments thereof, such as W-101, W-120 or CFK1-10a, in combination with one or more BMP receptor proteins, truncated BMP receptor proteins, or active fragments thereof, such as CFK1-23a or CFK1-43a. These cells or compositions may be produced by co-expressing each protein in a selected host cell and isolating the cells in a composition or, in the case where truncated receptor proteins are produced, by isolating the truncated receptor proteins from the culture medium.

As a further aspect of this invention a cell line is provided which comprises a first polynucleotide sequence encoding a first receptor protein, truncated receptor protein, or active fragment thereof and a second polynucleotide sequence encoding a second receptor protein, truncated receptor protein, or active fragment thereof, the sequences being under control of one or more suitable expression regulatory systems capable of co-expressing the receptor proteins. The cell line may be transfected with one or more than one polynucleotide molecule. Alternatively, the cell line may be a hybrid cell line created by cell fusion as described above.

Another aspect of the invention is a polynucleotide molecule or plasmid vector comprising a polynucleotide sequence encoding a first selected receptor protein, truncated receptor protein, or active fragment thereof and a polynucleotide sequence encoding a second selected receptor protein, truncated receptor protein, or active fragment thereof. The sequences are under the control of at least one suitable regulatory sequence capable of directing co-expression of each protein or active fragment. The molecule may contain a single transcription unit containing a copy of both genes, or more than one transcription unit, each containing a copy of a single gene.

One embodiment of the method of the present invention for producing compositions of cells or recombinant receptor proteins involves culturing a suitable cell line, which has been co-transfected with a DNA sequence coding for expression of a first receptor protein, truncated receptor protein, or active fragment thereof and a DNA sequence coding for expression of a second receptor protein, truncated receptor protein, or active fragment thereof, under the control of known regulatory sequences. The transformed host cells are cultured and the cells are isolated and purified to form compositions of transformed cells. In the embodiment wherein truncated receptor proteins are produced, the truncated receptor protein is recovered and purified from the culture medium and can be used to form compositions of truncated receptor protein.

In another embodiment of this method which is the presently preferred method of expression of the recombinant receptor proteins of this invention, a single host cell, e.g., a CHO DUKX cell, is co-transfected with a first DNA molecule containing a DNA sequence encoding one receptor protein, such as the receptor protein CFK1-10a, and a second DNA molecule containing a DNA sequence encoding a second selected receptor protein, such as the BMP receptor protein CFK1-23a or CFK1-43a. One or both plasmids contain a selectable marker that can be used to establish stable cell lines expressing the receptor proteins. These separate plasmids containing distinct receptor genes on separate transcription units are mixed and transfected into the CHO cells using conventional protocols. A ratio of plasmids that gives maximal expression of activity in the binding assay can be determined.

For example, equal ratios of a plasmid containing the first receptor protein gene and a dihydrofolate reductase (DHFR) marker gene and another plasmid containing a second receptor protein gene and a DHFR marker gene can be co-introduced into DHFR-deficient CHO cells, DUKX-BII, by calcium phosphate coprecipitation and transfection, electroporation, microinjection, protoplast fusion or lipofection. Individual DHFR expressing transformants are selected for growth in alpha media with dialyzed fetal calf serum by conventional means. DHFR+ cells containing increased gene copies can be selected for propagation in increasing concentrations of methotrexate (MTX) (e.g. sequential steps in 0.02, 0.1, 0.5 and 2.0 uM MTX) according to the procedures of Kaufman and Sharp, *J. Mol. Biol.*, 159:601–629 (1982); and Kaufman et al, *Mol. Cell Biol.*, 5:1750 (1983). Expression of or at least one receptor protein linked to DHFR should increase with increasing levels of MTX resistance. Cells that stably express either or both receptor protein/DHFR genes will survive. However at a high frequency, cell lines stably incorporate and express both plasmids that were present during the initial transfection. The conditioned medium is thereafter harvested and the receptor protein isolated by conventional methods and assayed for activity. This approach can be employed with DHFR-deficient cells.

As an alternative embodiment of this method, a DNA molecule containing one selected receptor gene may be transfected into a stable cell line which already expresses another selected receptor gene. For example, a stable CHO cell line expressing the gene for receptor CFK1-10a with the DHFR marker may be transfected with a plasmid containing the gene for receptor gene for CFK1-23a and a second selectable marker gene, e.g., neomycin resistance (Neo). After transfection, the cell is cultured and suitable cells selected by treatment with MTX and the antibiotic, G-418. Surviving cells are then screened for the expression of both receptor proteins. This expression system has the advantage of permitting a single step selection.

Alternative dual selection strategies using different cell lines or different markers can also be used. For example, the use of an adenosine deaminase (ADA) marker to amplify the second receptor gene in a stable CHO cell line expressing a different receptor with the DHFR marker may be preferable, since the level of expression can be increased using deoxycoformycin (DCF)-mediated gene amplification. Alternatively, any cell line expressing a receptor made by first using this marker can then be the recipient of a second receptor expression vector containing a distinct marker and selected for dual resistance and receptor coexpression.

Still another embodiment of a method of expressing the receptors of this invention includes transfecting the host cell with a single DNA molecule encoding multiple genes for expression either on a single transcription unit or on separate transcription units. Multicistronic expression involves multiple polypeptides encoded within a single transcript, which can be efficiently translated from vectors utilizing a leader sequence, e.g., from the EMC virus, from poliovirus, or from other conventional sources of leader sequences. Two receptor genes (Rx and Ry, respectively) and a selectable marker can be expressed within a single transcription unit. For example, vectors containing the configuration Rx-EMC-Ry-DHFR or Rx-EMC-Ry-EMC-DHFR can be transfected into CHO cells and selected and amplified using the DHFR marker. A plasmid may be constructed which contains DNA sequences encoding two different receptors, one or more marker genes and a suitable leader or regulatory sequence on a single transcription unit.

Similarly, host cells may be transfected with a single plasmid which contains separate transcription units for each receptor. A selectable marker, e.g., DHFR, can be contained on a another transcription unit, or alternatively as the second cistron on one or both of the receptor genes. These plasmids may be transfected into a selected host cell for expression of the receptors.

Another embodiment of this expression method involves cell fusion. Two stable cell lines which express selected receptors, such as a cell line transformed with a vector for CFK1-23a (e.g., pMV23a) and a cell line stably transformed with a vector for CFK1-43a (e.g., pMV43a), developed using the DHFR/MTX gene amplification system and expressing receptors at high levels, can be transfected with one of several dominant marker genes (e.g., $neo^r$, $hygromycin^r$, GPT). After sufficient time in coculture (approximately one day) one resultant cell line expressing one receptor and a dominant marker can be fused with a cell line expressing a different receptor and preferably a different marker using a fusigenic reagent, such as polyethylene glycol, Sendai virus or other known agent.

The resulting cell hybrids expressing both dominant markers and DHFR can be selected using the appropriate culture conditions, and screened for coexpression of the receptors, truncated receptors or their fragments. The selected hybrid cell contains sequences encoding both selected receptors, and both receptors will be retained within the membrane of the cell. Compositions of the cells expressing multiple receptors can be used in the methods of the present invention to interact with BMP. In the case where genes encoding truncated receptors are used, the truncated receptor is formed in the cell and then secreted. The truncated receptor protein is obtained from the conditioned medium and isolated and purified therefrom by conventional methods. The resulting receptor protein composition may be characterized by methods described herein and may be used in the methods of the present invention, for example, to compete with receptors present in cells for ligand binding and thus inhibit the activity of BMP.

Cell lines generated from the approaches described above can be used to produce co-expressed receptor polypeptides. The receptor proteins are retained within the membrane of the cells. Compositions of the cells may be used in order to increase response to BMP, for example to increase cartilage and/or bone formation. Compositions of the cells may be applied in conjunction with BMP.

Where truncated receptor polypeptides are produced, the receptor proteins are isolated from the cell medium in a form substantially free from other proteins with which they are co-produced as well as from other contaminants found in the host cells by conventional purification techniques. The presently preferred method of production is co-transfection of different vectors into CHO cells and methotrexate-mediated gene amplification. Stable cell lines may be used to generate conditioned media containing truncated receptor that can be purified and assayed for in vitro and in vivo activities. For example, the resulting truncated receptor-producing cell lines obtained by any of the methods described herein may be screened for activity by the binding assays described in Example VI, RNA expression, and protein expression by sodium dodecyl sulfate polyacrylamide gel electrophoresis (SDS-PAGE).

The above-described methods of co-expression of the receptors of this invention utilize suitable host cells or cell lines. Suitable cells preferably include mammalian cells, such as Chinese hamster ovary cells (CHO). The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7) :1750–1759 (1985) or Howley et al, U.S. Pat. No. 4,419,446. Other suitable mammalian cell lines are the CV-1 cell line, BHK cell lines and the 293 cell line.

Another aspect of the present invention provides DNA molecules or plasmid vectors for use in expression of these recombinant receptor proteins. These plasmid vectors may be constructed by resort to known methods and available components known to those of skill in the art. In general, to generate a vector useful in the methods of this invention, the DNA encoding the desired receptor protein, truncated receptor protein, or active fragment thereof, is transferred into one or more appropriate expression vectors suitable for the selected host cell.

It is presently contemplated that any expression vector suitable for efficient expression in mammalian cells may be employed to produce the recombinant receptor proteins of this invention in mammalian host cells. Preferably the vectors contain the selected receptor DNA sequences described above and in the Sequence Listings, which encode selected receptor proteins, or truncated receptor proteins. Alternatively, vectors incorporating modified sequences are also embodiments of the present invention and useful in the production of the vectors.

In addition to the specific vectors described above, one skilled in the art can construct mammalian expression vectors by employing the sequence of SEQ ID NO:1, 3, 5, 7, or 9 or other DNA sequences coding for receptor proteins, truncated receptor proteins, or active fragments thereof and known vectors, such as pCD [Okayama et al, *Mol. Cell Biol.,* 2:161–170 (1982)] and pJL3, pJL4 [Gough et al, *EMBO J.,* 4:645–653 (1985)]. The receptor DNA sequences can be modified by removing the non-coding nucleotides on the 5' and 3' ends of the coding region. The deleted non-coding nucleotides may or may not be replaced by other sequences known to be beneficial for expression. The transformation of these vectors into appropriate host cells as described above can produce desired receptor proteins.

One skilled in the art could manipulate the sequences of SEQ ID NO:1, 3, 5, 7, or 9 by eliminating or replacing the mammalian regulatory sequences flanking the coding sequence with e.g., yeast or insect regulatory sequences, to create vectors for intracellular or extracellular expression by yeast or insect cells. [See, e.g., procedures described in published European Patent Application 155,476] for expression in insect cells; and procedures described in published PCT application WO86/00639 and European Patent Application EPA 123,289 for expression in yeast cells].

Similarly, bacterial sequences and preference codons may replace sequences in the described and exemplified mammalian vectors to create suitable expression systems for use in the production of receptor proteins in the method described above. For example, the coding sequences could be further manipulated (e.g., ligated to other known linkers or modified by deleting non-coding sequences therefrom or altering nucleotides therein by other known techniques). The modified receptor coding sequences could then be inserted into a known bacterial vector using procedures such as described in T. Taniguchi et al, *Proc. Natl. Acad. Sci. USA,* 77:5230–5233 (1980). The exemplary bacterial vector could then be transformed into bacterial host cells and receptor proteins expressed thereby.

Other vectors useful in the methods of this invention may contain multiple genes in a single transcription unit. For example, a proposed plasmid contains the CFK1-10a receptor gene followed by the EMC leader sequence, followed by the CFK1-23a BMP receptor gene, followed by the DHFR marker gene. Another example contains the CFK1-23a BMP receptor gene, the EMC leader, the W101 serine/threonine kinase receptor gene, another EMC leader sequence and the DHFR marker gene. Alternatively, the vector may contain more than one transcription unit. As one example, the plasmid may contain a transcription unit for CFK1-23a BMP receptor gene and a separate transcription unit for CFK1-43a receptor gene, i.e., CFK1-23a-EMC-DHFR and CFK1-43a-EMC-DHFR. Alternatively, each transcription unit on the plasmid may contain a different marker gene. For example, the plasmid may contain CFK1-10a-EMC-Neo and CFK1-43a-EMC-DHFR. Of course, the above examples are not limiting. Other combinations (i.e., co-expression) of the receptors of the present invention are also within the invention.

Additionally the vectors also contain appropriate expression control sequences which are capable of directing the replication and expression of the receptor in the selected host cells. Useful regulatory sequences for such vectors are known to one of skill in the art and may be selected depending upon the selected host cells. Such selection is routine and does not form part of the present invention. Similarly, the vectors may contain one or more selection markers, such as the antibiotic resistance gene, Neo or selectable markers such as DHFR and ADA. The presently preferred marker gene is DHFR. These marker genes may also be selected by one of skill in the art.

The following examples illustrate practice of the present invention in recovering and characterizing the receptor proteins of the present invention and employing them to recover the corresponding human receptor proteins of the present invention, and in expressing the proteins via recombinant techniques.

Antibodies

As used herein, a molecule is said to be "BMP-like" if it exhibits at least one BMP-like activity. For the purposes of the invention, BMP-like activity includes the ability to bind to a truncated BMP receptor and to stimulate growth of BMP-dependent cell lines such as the W-20-17 cell line described in Example VIII. As used herein, the term "BMP-like monoclonal antibody" includes non-human BMP-like monoclonal antibodies, complementarity determining regions (CDRs) of the non-human BMP-like monoclonal antibodies, BMP recognition sites of the non-human BMP-like monoclonal antibodies, all engrafted forms of the BMP recognition sites of the non-human BMP-like monoclonal antibodies, and small peptide BMP analogues.

In accordance with the present invention, the term "BMP analogue" encompasses monoclonals, small peptides, and small molecules which possess BMP-like activity. For the purposes of the invention, BMP-like activity is defined as the ability to bind to the truncated BMP receptor and to stimulate growth of BMP-dependent cell lines such as the W-20-17 cell line described in Example VIII.

The BMP-like monoclonal antibodies of the invention may be molecularly altered to enhance their utility as human pharmaceuticals. For example, the CDRs of the BMP-like monoclonals comprise specific BMP receptor recognition sites, which are encompassed in the present invention. These CDRs may be engrafted onto human immunoglobulin framework regions to minimize antigenicity caused by the presence of non-human immunoglobulin regions, for example by the techniques disclosed in WO 91/09967. The BMP receptor recognition sites of the present invention may also be engrafted onto other protein frameworks to maximize the therapeutic efficiency of the BMP analogues developed therefrom. The CDRs of the BMP-like monoclonals may also be molecularly altered to form single chain antibodies.

The CDRs of the BMP-like monoclonal antibodies may also be used to make small peptide BMP analogues. The entire CDR may be present in the small peptide BMP analogues of the invention, or an BMP-like portion of the CDR may comprise such small peptide BMP analogues. Two or more CDRs may be joined in "head-to-head", "head-to-tail", or "tail-to-tail" orientation to form dimer or multimer small peptide BMP analogues. Since each BMP-like monoclonal antibody may contain multiple CDRs, a single CDR may be present in the small peptide BMP analogue or different BMP-like CDRs from one or more BMP-like monoclonal antibodies may be present. Non-naturally occurring, synthetic, and D-amino acids may be substituted for specific amino acids of the BMP-like CDRs.

The invention further encompasses peptides which specifically bind the truncated receptor and have BMP-like activity. These peptides may be, but are not exclusively, based on the sequence of the CDRs of BMP-like antibodies. The peptides may be "bridged" or "joined" to other peptides in multimeric structures of two peptides or more to elicit the BMP-like activity. The amino acids of the peptides may be, but are not exclusively, "unnatural" amino acids of, e.g., D-stereo-specificity or analogues of amino acids with other chemical groups attached to the peptide backbone. The peptides may also be cyclic in structure. A peptide as used herein is a molecule comprising of at least two amino acids and up to thirty amino acids.

The invention further encompasses small organic molecules, which may include amino acid-like molecules, which exhibit specific binding to the truncated human BMP receptor and which possess BMP-like activity. "Small organic molecules" are defined in accordance with the present invention as non-protein carbon-containing molecules of molecular weight less than 3000 which have been first identified for use as BMP analogues using the truncated receptor of the invention. The small organic molecules of the invention are capable of being incorporated into oral pharmaceuticals for treatment of bone and/or cartilage disorders.

Pharmaceutical compositions containing the BMP-like monoclonal antibodies, small peptide BMP analogues, or small organic molecules of the present invention are useful in treating a variety of bone and/or cartilage disorders of diverse etiologies. Such pharmaceutical compositions may also contain pharmaceutically acceptable carriers, diluents, fillers, salts, buffers, stabilizers, and/or other materials well known in the art. The term "pharmaceutically acceptable" means a non-toxic material that does not interfere with the effectiveness of the biological activity of the active ingredient(s). The characteristics of the carrier or other material will depend on the route of administration.

Administration of the BMP-like monoclonal antibodies, small peptide BMP analogues or small organic molecules of the invention can be carried out in a variety of conventional ways, including via matrices and/or carriers such as are disclosed in U.S. Pat. No. 5,171,579. For the BMP-like monoclonal antibodies, intravenous administration to the patient is preferred. Cutaneous or subcutaneous injection may also be employed for administration of the monoclonal antibody embodiment of the invention. Oral administration is preferred for administration of the small peptide and small organic molecule BMP analogue embodiments of the invention.

The amount of BMP-like monoclonal antibody, small peptide analogue or small organic molecule in the pharmaceutical composition of the present invention will depend upon the nature and severity of the condition being treated, and on the nature of prior treatments which the patient has undergone. Ultimately, the attending physician will decide the amount of BMP analogue with which to treat each individual patient. It is contemplated that the various pharmaceutical compositions of the present invention should contain about 0.1 µg to about 100 µg of BMP analogue molecule per kg body weight.

EXAMPLES

Example I

Identification of the Murine KDA-B5 Sequence

Two peptide sequences were derived from the amino acid sequence of the activin receptor in the region described as the kinase domain of the molecule (Mathews et al., Cell, 65:973–982(1991)). These particular sequences were selected on the basis of a comparison between the amino acid sequence of the Daf-1 gene product and the activin receptor and are predicted to be conserved in other serine threonine kinase receptor molecules. The two peptide sequences selected were:

1. Asn-Glu-Tyr-Val-Ala-Val-Lys  (SEQ ID NO:18)

2. His-Arg-Asp-Ile-Lys-Ser      (SEQ ID NO:19)

The following oligonucleotide primer was designed on the basis of amino acid sequence #1 and synthesized on an automated DNA synthesizer.

```
Oligonucleotide primer A:  GCGGATCCGARTAYGTHGCHGTNAAR  (SEQ ID NO:20)
```

The first 8 nucleotides of this primer (underlined) comprise a recognition sequence for the restriction endonuclease BamHI in order to facilitate subsequent manipulations of amplified DNA products and are not derived from amino acid sequence #1.

The following oligonucleotide primers were designed on the basis of amino acid sequence #2 and synthesized on an automated DNA synthesizer.

```
Oligonucleotide primer B:  GACTCTAGARCTYTTDATRTCYCTRTG  (SEQ ID NO:21)

Oligonucleotide primer C:  GACTCTAGARCTYTTDATRTCNCGRTG  (SEQ ID NO:22)

Oligonucleotide primer D:  GACTCTAGANGAYTTDATRTCYCTRTG  (SEQ ID NO:23)

Oligonucleotide primer E:  GACTCTAGANGAYTTDATRTCNCGRTG  (SEQ ID NO:24)
```

The first 9 nucleotides of primers B through E (underlined) comprise a recognition sequence for the restriction endonuclease XbaI in order to facilitate subsequent manipulations of amplified DNA products and are not derived from amino acid sequence #2.

The standard nucleotide symbols in the above identified primers are as follows: A=adenosine, C=cytosine, G=guanine, T=thymine, R=adenosine or guanine, Y=cytosine or thymine and D=guanine, adenosine or thymine.

These oligonucleotides have been selected for their predicted ability to specifically amplify serine/threonine kinase domain encoding sequences similar to those found in the activin receptor sequence. Since activin and the BMP molecules are members of the large TGF-β superfamily of growth and differentiation factors we predict that their corresponding receptors may also be related to each other in structure and primary amino acid sequence. The TGF-β type II receptor sequence (Lin et al., Cell, 68:775–785 (1992)) indicates that like the activin receptor it is also a serine threonine kinase. On the basis of the above described relationships, we predicted that these degenerate oligonucleotides will specifically amplify sequences encoding fragments of other serine/threonine kinase receptor molecules including activin receptors, TGF-β receptors and BMP receptors.

The BMP-2 responsive mouse cell line W-20-17 was selected as a source of mRNA which we would predict to contain molecules that are capable of encoding BMP receptors. Total RNA was extracted from W-20-17 cells using established procedures known to those skilled in the art, and mRNA was subsequently selected for by oligo (dT) cellulose chromatography. 10 ng of the W-20-17 mRNA was utilized as a template to synthesize first strand cDNA in a reaction mixture (20 µl total volume) containing 1 mM each deoxynucleotide triphosphate (dATP, dGTP, dCTP, dTTP), 10 mM Tris-HCl (pH 8.3), 50 mM KCl, 5 mM MgCl$_2$, 1 U/µl RNase inhibitor, 2.5 U/µl reverse transcriptase, 2.5 µM random hexmers and 20 ng of the W-20-17 mRNA described above. This reaction mixture was incubated for 10 minutes at room temperature, followed by 15 minutes at 42° C. and then 5 minutes at 99 C. The completed first strand cDNA reaction was then placed at 4° C.

Oligonucleotide combinations consisting of oligonucleotide primer A paired with either oligonucleotide primer B, C, D or E were utilized as primers to allow the amplification of specific nucleotide sequences from the first strand W-20-17 cDNA template described above. The amplification reaction was performed by adjusting the first strand cDNA reaction described above (20 µl) to a volume of 100 µl in order to bring the components of the reaction buffer to the following final concentrations: 2 mM MgCl$_2$, 10 mM Tris-HCl (pH 8.3), 50 mM KCl, 2.5 U/100 µl Taq DNA polymerase, 1 pM/µl oligonucleotide primer A and 1 pM/µl of either oligonucleotide primer B, C, D or E. The entire reaction mixture was then incubated at 95° C. for two minutes and then subjected to thermal cycling in the following manner: 1 minute at 95° C., 1 minute at 40° C. and 1 minute at 72° C. for forty cycles; followed by a 7 minute incubation at 72° C., after which the completed reaction is held at 4° C.

The DNA which was specifically amplified by this reaction was ethanol precipitated, digested with the restriction endonucleases BamHI and XbaI and subjected to agarose gel electrophoresis. Regions of the gel in which DNA bands were evident were excised and the DNA contained within was eluted with a QIAEX Gel Extraction Kit (Qiagen catalog no: 20020) according to the instructions supplied by the manufacturer. The gel-extracted DNA fragments were subcloned into the plasmid vector pGEM-3 between the BamHI and XbaI sites of the polylinker. DNA sequence analysis of one of the resulting subclones named KDA-B5 indicated that the specifically amplified DNA sequence insert encodes an amino acid sequence homologous to the corresponding region of the activin receptor and Daf-1 gene product kinase domains in the region between where the oligonucleotide primers A, B, C, D and E were designed (as described in the beginning of this section). The amino acid sequence encoded by this region of the specifically amplified KDA-B5 sequence is 41% and 47% identical to the corresponding regions of the activin receptor and Daf-1 kinase domains, respectively.

The DNA sequence and derived amino acid sequence of the specifically amplified KDA-B5 DNA fragment are set forth in SEQ ID NO:11 and SEQ ID NO:12, respectively.

Nucleotides 1–24 of the sequence set forth in SEQ ID NO:11 comprise a portion of the oligonucleotide primer A and nucleotides 319–341 comprise a portion of the reverse compliment of oligonucleotide primer B utilized to perform the specific amplification reaction. Due to the function of oligonucleotides A and B in initiating the amplification reaction, they may not correspond exactly to the actual sequence encoding the mouse KDA-B5 protein and are therefore not translated in the above amino acid derivation.

Example II

Isolation of W101 and W120 Clones from a W-20-17 cDNA Library

The 341 bp sequence of the KDA-B5 insert set forth in SEQ ID NO:11 was utilized as a probe to screen a W-20-17 cDNA library under reduced stringency conditions (4×SSC, 0.1% SDS at 60° C.) in an attempt to isolate other mouse sequences related to KDA-B5 in the following manner.

1,000,000 recombinants of a W-20-17 (Thies et al., *Endocrinology*, 130:1318–1324 (1992)) cDNA library constructed in the vector λZAPII were plated at a density of 20,000 recombinant bacteriophage plaques per plate on 100 plates. Duplicate nitrocellulose replicas of the plates were made. A DNA fragment corresponding to the 341 bp sequence of the KDA-B5 insert set forth in SEQ ID NO:11 was $^{32}$P-labelled by the random priming procedure of Feinberg et al., Anal. Biochem. 132:6–13 (1983), and hybridized to one set of filters in standard hybridization buffer (SHB: 5×SSC, 0.1% SDS, 5×Denhardt's, 100 μg/ml salmon sperm DNA) at 60° C. for 2 days. The other set of filters was hybridized to a DNA probe corresponding to nucleotides # 710 to 1044 of the published sequence of the activin receptor (Mathews et al., *Cell*, 65:973–982 (1991)) under the same conditions described for the first set. This region of the activin receptor kinase domain corresponds to the DNA sequence of the KDA-B5 insert. The filters were washed under reduced stringency conditions (4×SSC, 0.1% SDS at 60° C.). 13 positively hybrdizing recombinant bacteriophage plaques were selected and replated for secondaries. Duplicate nitrocellulose replicas of the recombinant plaques from these plates were made. Again, one set of filters was hybridized to the KDA-B5 probe and the other set to the activin receptor probe as described above in the primary screen (in SHB at 60° C. for 2 days). Both sets of filters were washed under the reduced stringency conditions described above (4×SSC, 0.1% SDS at 60° C.). Two recombinants which hybridized strongly to the KDA-B5 probe but not to the corresponding activin receptor probe were selected for further analysis. These two cDNA clones, designated W-101 and W-120, were plaque purified and their inserts were transferred to the plasmid Bluescript SK (+/−) according to the in vivo excision protocol described by the manufacturer (Stratagene). DNA sequence analysis of these recombinants indicated that they encode proteins homologous to the activin receptor and the Daf-1 gene product. The DNA sequence and derived amino acid sequence of a portion of pMT101 (ATCC 69379) is set forth in SEQ ID NO:7 and SEQ ID NO:8, respectively.

The nucleotide sequence of clone W-101 indicates that it encodes a partial polypeptide of 467 amino acids comprising the carboxy-terminal portion of the murine receptor molecule W-101. A random primed cDNA library was made from W-20-17 mRNA using a random hexmer pd(N)$_6$ (Pharmacia/LKB catalog # 27-2166-01) to prime synthesis of first strand cDNA from the W-20-17 mRNA template. The library was screened with a 30 base oligonucleotide corresponding to nucleotide # 245 to 274 of SEQ ID NO:7. The DNA sequence utilized to design this oligonucleotide probe was derived from the coding sequence of clone W-101. Hybridization was performed in SHB at 65° C. and stringent wash conditions of 0.2×SSC, 0.1% SDS AT 65° C. were employed to remove non-specifically bound probe. The DNA insert of one of these clones, WR9, was characterized by DNA sequence analysis and determined to contain additional 5' coding sequences of the murine W-101 receptor not present in the original cDNA clone described above. The 0.7 kb insert of the W9 clone however lacks sequences which encode the C-terminal region of the murine W-101 receptor protein. In order to construct a cDNA sequence which would encode the complete W-101 receptor protein, DNA sequences from both the original oligo (dT) and the random primed clone W9 have been joined at a common BstEII restriction endonuclease site. The sequence set forth in SEQ ID NO:7 contains an open reading frame of 1515 base pairs which encodes the complete 505 amino acid murine W-101 receptor protein. Nucleotides 1-660 of the sequence set forth in SEQ ID NO:7 are derived from the W9 cDNA clone while the remaining sequence (nucleotides 661–1648 are derived from the oligo (dT) primed cDNA clone W-101. The BstEII restriction endonuclease recognition sequence GGTNACC (located at position 660–666) facilitated the construction of this chimeric cDNA sequence. This construction was accomplished by digesting clone W-101 and clone W9 with the restriction endonuclease BstEII resulting in the linearization of each plasmid at the common BstEII site of their respective inserts. The two linearized plasmids were gel isolated, then ligated together at this site and digested with the restriction endonuclease SalI in order to separate the sequence set forth in SEQ ID NO:7 from the plasmid vector sequences (pBluescript). The DNA fragments resulting from this sequential ligation and SalI digest were electrophoresed on an agarose gel. A region containing a DNA fragment of approximately 2.3 kb, comprising 660 bp of the 5' end of the W9 cDNA and approximately 1.64 kb of the 3' end of the original W-101 cDNA, was excised from the gel and the DNA contained therein was eluted with a QIAEX Gel Extraction Kit (Qiagen catalog no: 20020) according to the instructions supplied by the manufacturer. The resulting DNA fragment which comprises the sequence set forth in SEQ ID NO:7 (encoding the complete murine W101 receptor protein) was subcloned into the mammalian cell expression vector pMT3 at the Sal I site of the polylinker region. This plasmid is designated pMT101.

The nucleotide sequence of a portion of the insert of cDNA clone W120 is set forth in SEQ ID NO:9. The presumed initiator methionine encoding sequence is preceded by 68 bp of 5' untranslated sequence and defines an open reading frame of 1509 bp which encodes the complete 503 amino acid murine receptor molecule W-120. The stop codon is followed by at least 203 bp of 3' untranslated sequence. The insert of clone W120 comprising the sequence set forth in SEQ ID NO:9 is excised from the pBluescript plasmid with the restriction endonuclease EcoRI and transferred to the mammalian cell expression vector pMT3 at the EcoRI site of the polylinker region. This plasmid is designated pMT120E and has been deposited with the American Type Culture Collection (ATCC #69377).

Example III

Isolation of CFK1-10a, CFK1-23a and CFK1-43a from a CFK1 cDNA Library

Another BMP-2 responsive cell line CFK1 [Bernier and Goltzman, *J. Cell. Physiol.*, 152:317 (1992)] was selected as a source of mRNA which would be predicted to contain molecules capable of encoding BMP receptors and additional serine/threonine kinase encoding sequences related to the TGF-β receptor, the activin receptor, daf-1, W-101 and W-120.

1×10$^6$ recombinants of a CFK1 cDNA library constructed in the vector λZAPII were plated at a density of 20,000 recombinant bacteriophage plaques per plate on 50 plates. Duplicate nitrocellulose replicas of the plates were made. A 645 base pair DNA fragment of the W-101 cDNA insert corresponding to nucleotides #828–#1472 of SEQ ID NO:7 was $^{32}$P-labelled by the random priming procedure of Feinberg et al., Anal. Biochem., 132:6–13 (1983) and hybridized to both sets of filters in SHB at 60° C. for two days. The filters were washed under reduced stringency conditions (4×SSC, 0.1% SDS at 60° C.). Many duplicate hybridizing recombinants of various intensities (approximately 200) were noted. 27 bacteriophage plaques which were representative of the broad range of hybridization intensity were plaque purified and their inserts were transferred to the plasmid pBluescript SK (+/−) according to the in vivo excision protocol described by the manufacturer (Stratagene). DNA sequence analysis of several recombinants indicated that they encode proteins homologous to the activin receptor, Daf-1 and other receptor proteins of the serine/threonine kinase receptor family.

The nucleotide sequence of clone CFK1-10a comprises an open reading frame of 1527 bp, encoding a CFK1-10a receptor protein of 509 amino acids. The encoded 509 amino acid CFK1-10a receptor protein is contemplated to be the primary translation product, as the coding sequence is preceded by 458 bp of 5' untranslated sequence with stop codons in all three reading frames. The DNA and derived amino acid sequence of the majority of the insert of CFK1-10a (ATCC # 69380) is set forth in SEQ ID NO:5.

Based on the knowledge of other serine/threonine kinase receptor proteins, the encoded 509 amino acid CFK1-10a has the characteristic features of serine/threonine kinase receptors, particularly those capable of recognizing ligands of the TGF-β/BMP superfamily of growth and differentiation factors. This molecule encodes a full length receptor molecule with a characteristic hydrophobic leader sequence which targets the ligand binding domain of the protein to the extracellular space, a transmembrane region which anchors the complete receptor molecule in the cell membrane allowing the positioning of the serine threonine kinase domain within the intracellular space. The ligand binding domain of the CFK1-10a receptor molecule of the invention exhibits a pattern of cysteine conservation noted for other receptors capable of recognizing ligands of the TGF-β/BMP superfamily of growth and differentiation factors. The region of the CFK1-10 a receptor protein corresponding to the intracellular serine threonine kinase domain exhibits a significant degree of amino acid sequence identity to the corresponding domain of other receptors of this family as follows. TGF-β type II receptor (Genbank Accession No. M85079), 35%; activin type II receptor (Genbank Accession No. M65287), 40%; activin type IIB receptor (Genbank Accession No. M84120), 38%; and Daf-1 (Genbank Accession No. A35103), 39%. The 3.2 kb insert of the CFK1-10a cDNA clone is excised with the restriction endonuclease NotI and transferred to the mammalian cell expression vector pMV2 at the NotI site of the polylinker. This plasmid is designated CFK1-10a/Not-4.

The CFK1-10a receptor of the present invention is homologous to a human serine/threonine kinase receptor mRNA entered into Genbank, accession number L02911, for which no ligand was identified. This receptor protein is also homologous to the reported murine type I TGF-β receptor, Ebner et al., *Science,* 260:1344–1348 (1993)(Genbank Accession No. L15436).

The nucleotide sequence of clone CFK1-23a (ATCC # 69378) comprises an open reading frame of 1596 bp, encoding a CFK1-23a receptor protein of 532 amino acids. The encoded 532 amino acid CFK1-23a receptor protein is contemplated to be the primary translation product. The coding sequence is preceded by 60 bp of 5' untranslated sequence. The DNA and derived amino acid sequence of the majority of the insert of CFK1-23a is set forth in SEQ ID NO:1.

Based on the knowledge of other serine/threonine kinase receptor proteins, the encoded 532 amino acid CFK1-23a has the characteristic features of serine/threonine kinase receptors, particularly those capable of recognizing ligands of the TGF-β/BMP superfamily of growth and differentiation factors. The region of the CFK1-23a receptor protein corresponding to the intracellular serine threonine kinase domain exhibits a significant degree of amino acid sequence identity to the corresponding domain of other receptors of this family as follows: TGF-β type II receptor (Genbank Accession No. M85079), 35%; activin type II receptor (Genbank Accession No. M65287), 41%; activin type IIB receptor (Genbank Accession No. M84120), 39%; and Daf-1 (Genbank Accession No. A35103), 39%. The 2.8 kb insert of the CFK1-23a cDNA clone is excised with the restriction endonuclease EcoRI and transferred to the mammalian cell expression vector pMV2 at the EcoRI site of the polylinker. This plasmid is designated pMV23a.

The nucleotide sequence of clone CFK1-43a comprises an open reading frame of 1506 bp, encoding a CFK1-43a receptor protein of 502 amino acids. The encoded 502 amino acid CFK1-43a receptor protein is contemplated to be the primary translation product, as the coding sequence is preceded by 239 bp of 5' untranslated sequence with stop codons in all three reading frames. The DNA and derived amino acid sequence of the insert of CFK1-43a (ATCC # 69381) is set forth in SEQ ID NO:3.

Based on the knowledge of other serine/threonine kinase receptor proteins, the encoded 502 amino acid CFK1-43a has the characteristic features of serine/threonine kinase receptors, particularly those capable of recognizing ligands of the TGF-β/BMP superfamily of growth and differentiation factors. The region of the CFK1-43a receptor protein corresponding to the intracellular serine threonine kinase domain exhibits a significant degree of amino acid sequence identity to the corresponding domain of other receptors of this family as follows: TGF-β type II receptor (Genbank Accession No. M85079), 35%; activin type II receptor (Genbank Accession No. M65287), 41%; activin type IIB receptor (Genbank Accession No. M84120), 40%; and Daf-1 (Genbank Accession No. A35103), 38%. The 2.1 kb insert of the CFK1-43a cDNA clone is excised with the restriction endonuclease EcoRI and transferred to the mammalian cell expression vector pMV2 at the EcoRI site of the polylinker. This plasmid is designated pMV43a.

The CFK1-43a receptor of the invention is homologous to a chicken serine/threonine kinase receptor mRNA, entered into Genbank Accession No. D 13432, for which no ligand has been identified.

Example IV

Screening for Human BMP Receptors

Mouse and/or rat BMP receptor genes are presumed to be significantly homologous. Therefore, the mouse coding sequences of W-101 or W-120 or portions thereof can be used to screen a human genomic or human cDNA library or as probes to identify a human cell line or tissue which synthesizes the analogous human BMP receptor proteins. In a similar manner, the rat coding sequences of CFK1-10a, CFK1-23a or CFK1-43a or portions thereof can be utilized to screen human libraries or as probes to identify a human cell line or tissue which synthesize the analogous human BMP receptor proteins. A human genomic library may be screened with such probes, and presumptive positively hybridizing recombinant clones isolated and DNA sequence obtained. Evidence that such recombinants encode portions of the corresponding human BMP receptor proteins relies on the murine or rat/human DNA, protein and gene structure homologies.

Once a recombinant bacteriophage or plasmid containing DNA encoding a portion of a human BMP receptor molecule is obtained, the human coding sequence can be used to identify a human cell line or tissue which synthesizes the corresponding human BMP receptor mRNA. Alternatively, the mouse or rat BMP receptor encoding sequence can be utilized as a probe to identify such a human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence from the mouse, rat or human BMP receptor. Alternatively, the mouse or rat BMP receptor coding sequence is used to design oligonucleotide primers which will specifically amplify a portion of the BMP receptor encoding sequence located in the region between the primers utilized to perform the specific amplification reaction. It is contemplated that mouse, rat and human BMP receptor coding sequences would be sufficiently homologous to allow one to specifically amplify corresponding human BMP receptor encoding sequences from mRNA, cDNA or genomic DNA templates. Once a positive source has been identified by one of these above described methods, mRNA is selected by oligo (dT) cellulose chromatography and cDNA is synthesized and cloned in a suitable vector (ie. $\lambda$gt10, $\lambda$ZAPII or other vectors known to those skilled in the art) by established techniques. It is also possible to perform the oligonucleotide primer-directed amplification reaction, described above, directly on a pre-established human cDNA or genomic library which has been cloned into a $\lambda$ bacteriophage or plasmid vector. In such cases, a library which yields a specifically amplified DNA product encoding a portion of human BMP receptor protein could be screened directly, utilizing the fragment of amplified BMP receptor encoding DNA as a probe.

Example V

Expression of BMP Receptors

In order to produce mouse, rat, human or other mammalian BMP receptor proteins, the DNA encoding it is transferred into an appropriate expression vector (as described above for W-101, W-120, CFK1-10a, CFK1-23a and CFK1-43a) and introduced into mammalian cells or other preferred eukaryotic or prokaryotic hosts by conventional genetic engineering techniques. The DNA sequences encoding BMP receptor protein may be inserted into a vector suitable for a particular host cell, as described above. The preferred expression system for recombinant human BMP receptor proteins is contemplated to be stably transformed mammalian cells.

A. COS Cell Expression

As one specific example of expressing a serine/threonine kinase receptor protein of the invention, the insert of CFK1-23a (containing the full length BMP receptor cDNA for CFK1-23a) is released from the vector arms by digestion with EcoRI and subcloned into the EcoRI site of the mammalian expression vector, pMV2, a derivative of pMT2, which has been deposited with ATCC wunder the accession number ATCC 67122, though other derivatives thereof, such as pMT3, may also be suitable. Plasmid DNA from this subclone is transfected into COS cells by the DEAE-dextran procedure [Sompayrac and Danna *PNAS* 78:7575–7578 (1981); Luthman and Magnusson, *Nucl. Acids Res.* 11: 1295–1308 (1983)] and the cells are cultured. Serum-free 24 hr. conditioned medium is collected from the cells starting 40–70 hr. post-transfection.

B. CHO Cell Expression (1) Serine/threonine kinase Receptor Expression in CHO Cells In order to achieve high levels of serine/threonine kinase receptor protein expression, each of the DNA sequences of SEQ ID NO:1, SEQ ID NO:3, SEQ ID NO:5, SEQ ID NO:7 or SEQ ID NO:9 are inserted into a eucaryotic expression vector, i.e., pMV2 or pMT3, stably introduced into CHO cells and amplified to high copy number by methotrexate selection of DHFR [Kaufman et al., *EMBO J.* 6:189 (1987)]. The transformed cells are cultured and the expressed receptor proteins remain associated with the cell membrane of the transformed cell. Recombinant receptor proteins of the present invention can be dissociated from the transformed cell membrane and then are recovered and purified from other contaminants present.

A serine/threonine kinase receptor protein of the invention is expressed in CHO cells by releasing the insert of cloned CFK1-43a described above with EcoRI. The insert is subcloned into the EcoRI cloning site of the mammalian expression vector, pMV2 described above, though derivatives thereof, i.e., pMT3, may also be suitable.

Methods for producing heterologous protein from CHO cells are known in the art and are described above, at pages 16 through 19.

Example VI

Binding Assays to Determine Affinity of Cloned Receptors for Different TGF-$\beta$/BMP Superfamily Ligands A BMP receptor of the invention can be defined by a protein possessing the ability to bind a particular BMP at a greater binding affinity than TGF-$\beta$, activin, inhibin or other members of the TGF-$\beta$ family of growth and differentiation factors. The BMP receptors of the present invention bind specifically to a particular BMP such that approximately a 100-fold excess of a competitive ligand such as TGF-$\beta$ or activin will not significantly displace the BMP. Specific binding of BMPs to a particular BMP receptor of the invention can be demonstrated by transfecting an expression plasmid containing DNA sequences encoding the particular BMP receptor protein of interest into COS cells and allowing for the transient expression of the BMP receptor protein on the cell surface. Individual BMPs, heterodimeric BMPs or other proteins of the TGF-$\beta$ superfamily are bound to BMP receptor expressing COS cells and the cells are analyzed for their ability to bind specifically to a BMP molecule or particular set of BMP proteins with greater affinity than to TGF-$\beta$ or other members of the TGF-$\beta$ superfamily. Such binding assays may be performed in the following manner:

COS cells that have been transfected with an expression vector containing the particular BMP receptor coding sequence of interest (e.g., pMT101, pMT120, CFK1-10a/Not-4, pMV23a or pMV43a) are plated on gelatinized 6 well plates and preincubated at 37° C. for 60 minutes in binding buffer (128 mM NaCl, 5 mM KCl, 5 mM MgSO$_4$, 1.2 mM CaCl$^2$, 50 mM HEPES and 5 mg/ml BSA, pH 7.5). The preincubated COS cells are washed and incubated in binding buffer supplemented with 10 mM KCN and 2 mM NaF for 10 minutes prior to the addition of BMP-4 and/or [$^{125}$I] BMP-4. BMP-4 binding is allowed to equilibrate at 37° C. for 60 minutes. Following binding, the cells are washed twice with ice-cold binding buffer and solubilized with 1% Triton X-100, 10% glycerol, 25 mM HEPES and 1 mg/ml BSA, pH 7.5, as described by Massague [Meth. Enzymol. 146: 174–195 (1987)]. Radioactivity is then determined in a gamma counter.

Example VII

Production of Truncated Receptor Proteins for Production of Truncated Protein Truncated receptor proteins of the invention preferably comprise the ligand binding domain but not the transmembrane and serine/threonine kinase domains of the receptor proteins. Such truncated receptor proteins can be expressed in mammalian cells in a manner that the truncated receptor proteins will be secreted into the supernatant rather than be expressed on the surface of the host cell. DNA sequences encoding the ligand binding domain of each receptor protein of the invention can be isolated from DNA sequences encoding the transmembrane and serine/threonine kinase domains of each corresponding receptor protein of the invention and inserted into vectors which will allow for the production of truncated receptor proteins in mammalian cells. Alternatively, the DNA sequences encoding the truncated receptor proteins may be isolated and inserted into suitable vectors for expression in bacterial, insect, viral and yeast cells. Such vectors are known to those skilled in the art and are described elsewhere in this application.

In a preferred embodiment, DNA sequences comprising nucleotides # 61 through # 507 of SEQ ID NO:1 encoding amino acids # 1 through 149 of the CFK1-23a receptor protein of the invention (SEQ ID NO:2) can be specifically amplified and the resulting DNA sequence can be inserted into a standard mammalian cell expression vector (i.e., pMV2 or pMT3). This specific amplification can be performed in the following manner:

Oligonucleotide primers comprising the nucleotide sequence # 1 through # 20 of SEQ ID NO:1 and a separate primer comprising the complimentary strand of nucleotide sequence # 488 through 507 of SEQ ID NO:1 are synthesized on an automated DNA synthesizer. Additionally these oligonucleotides could be designed to include recognition sequences of restriction endonucleases known by those skilled in the art (ie. BamHI, EcoRI, XbaI etc.) to be useful in the manipulation of amplified DNA products and the facilitation of their insertion into plasmid vectors. Furthermore the primer comprising nucleotides # 488 through 507 could also include a trinucleotide sequence corresponding to a translational stop codon (ie. TAA, TAG or TGA) in place of nucleotides # 583 through 585 of SEQ ID NO:1. The oligonucleotide comprising nucleotides # 488 through 507 would be designed on the basis of the antisense (complementary) strand of this region of SEQ ID NO:1. and in combination with an oligonucleotide comprising nucleotides # 1 through 20 of the sense (coding) strand of SEQ ID NO:1 could be used to specifically amplify a DNA fragment comprising nucleotides #1 through # 507 of SEQ ID NO:1. This DNA fragment will encode a truncated receptor protein of the invention. The DNA fragment encoding the truncated receptor protein of the invention can be produced by specifically amplifying the sequence comprising nucleotides # 1 through # 507 of SEQ ID NO:1 through the use of a clone encoding the complete receptor of the invention, such as pMV23a, as a template. This specific DNA amplification reaction can be performed as follows: approximately 1 ng of template DNA, such as pMV23a is combined with 100 pM of an oligonucleotide comprising nucleotides #1 through 20 and 100 pM of an oligonucleotide comprising the complementary strand of nucleotides # 488 through 507 in a 100 µl reaction mixture consisting of 10 mM Tris-HCl (pH 8.3), 50 mM KCl, 1.5 mM $MgCl_2$ 200 µM each deoxynucleotide triphosphate and 2.5 units of Taq DNA polymerase. The entire reaction is then incubated at 95° C. for two minutes and then subjected tom thermal cycling in the following manner: 1 minute at 95° C., 1 minute at 40° C. and 1 minute at 72° C. for twenty-five to forty cycles; followed by a 7 minute incubation at 72° C., after which the completed reaction is held at 4° C.

The DNA fragment which is specifically amplified by this reaction is ethanol precipitated, digested with the appropriate restriction endonucleases in the cases where restriction endonuclease recognition sequences have been added to the oligonucleotides utilized to prime the synthesis of the amplified DNA fragment (described above), and subjected to agarose electrophoresis. A region of the gel in which a DNA band of the expected size is evident is excised and subcloned into a plasmid vector. Alternatively this specifically amplified DNA fragment encoding a truncated receptor protein of the invention could be subclone directly into a standard mammalian cell expression vector such as pMT3 or other such vectors known to those skilled in the art.

Similar manipulations could be performed as above, in order to isolate and express other truncated receptor proteins of the invention.

For example, DNA sequences comprising nucleotides #247 through 618 of SEQ ID NO:3 encoding amino acids # 1 through 124 of the CFK1-43a BMP receptor of the invention (SEQ ID NO:4) can be specifically amplified to produce a DNA fragment comprising nucleotides # 247 through 618 of SEQ ID NO:3 which will encode another truncated BMP receptor protein. These sequences will encode the ligand binding domain of the CFK1-43a BMP receptor but will not encode the transmembrane and serine/threonine kinase domains of the corresponding receptor protein. When inserted into an appropriate expression vector and transfected into the appropriate host cell, this construct will allow the production of a truncated BMP receptor protein which will be secreted into the medium rather than be expressed on the surface of the host cell. This specific amplification reaction can be performed in a similar manner to that described above with respect to the truncated CFK1-23a BMP receptor protein. In this case, oligonucleotides comprising the nucleotide sequence #247 through 266 of SEQ ID NO:3 and a separate oligonucleotide primer comprising the complementary strand of nucleotide sequence # 599 through 618 of SEQ ID NO:3 are utilized to specifically amplify a DNA fragment comprising nucleotides # 247 through 618 of SEQ ID NO:3. These oligonucleotides and a template DNA encoding the corresponding BMP receptor protein of the invention such as pMV43a, are substituted in the specific DNA amplification reaction mixture described earlier.

Additionally, other serine/threonine kinase receptors of the invention such as W-101, W-120 or CFK1-10a can be produced in a truncated form. The truncated forms of these receptor molecules can be expressed in mammalian cells in a manner that the corresponding truncated proteins will be secreted into the culture media rather than be expressed on the surface of the host cell. The expression of these soluble receptor proteins can be accomplished through the amplification of DNA fragments encoding the ligand binding domain, but not the transmembrane and serine/threonine kinase domains, of each respective serine/threonine kinase receptor molecule as described above for the truncated BMP receptor proteins.

Example VIII

W-20-17 Bioassays

A. Description of W-20-17 Cells

Use of the W-20-17 bone marrow stromal cells as an indicator cell line is based upon the conversion of these cells to osteoblast-like cells after treatment with a BMP protein [Thies et al, *Journal of Bone and Mineral Research*, 5:305 (1990); and Thies et al, *Endocrinology*, 130:1318 (1992)]. Specifically, W-20-17 cells are a clonal bone marrow stromal cell line derived from adult mice by researchers in the laboratory of Dr. D. Nathan, Children's Hospital, Boston, Mass. Treatment of W-20-17 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20-17 stromal cells to osteoblast-like cells only upon treatment with BMPs. In this manner, the in vitro activities displayed by BMP treated W-20-17 cells correlate with the in vivo bone forming activity known for BMPs.

Below two in vitro assays useful in comparison of BMP activities of formulations of BMPs with the activity of known BMPs are described.

B. W-20-17 Alkaline Phosphatase Assay Protocol

W-20-17 cells are plated into 96 well tissue culture plates at a density of 10,000 cells per well in 200 µl of media (DME with 10% heat inactivated fetal calf serum, 2 mM glutamine and 100 Units/ml penicillin+100 µg/ml streptomycin. The cells are allowed to attach overnight in a 95% air, 5% $CO_2$ incubator at 37° C.

The 200 µl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20-17 indicator cells. After the 24 hours, plates are removed from the 37° C. incubator and the test media are removed from the cells.

The W-20-17 cell layers are washed 3 times with 200 µl per well of calcium/magnesium free phosphate buffered saline and these washes are discarded.

50 µl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 µl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 µl of 0.2 N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table 2.

Absorbance values for known amounts of BMPs can be determined and converted to µmoles of p-nitrophenol phosphate cleaved per unit time as shown in Table 3.

TABLE 2

Absorbance Values for Known Standards of P-Nitrophenol Phosphate

| P-nitrophenol phosphate umoles | Mean absorbance (405 nm) |
|---|---|
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

TABLE 3

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of new BMP formulations to known active BMP formulations.

C. Osteocalcin RIA Protocol

W-20-17 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20-17 cells for a total of 96 hours with replacement at 48 hours by the same test medias.

At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20-17 cells in response to BMP treatment is carried out as described in the protocol provided by the manufacturer.

Example IX

Rat Ectopic Study

Twenty four Long-Evans male rats are divided into 6 test groups. Each receives a subcutaneous implant, 200 uL in size, with either a 0 or 20 ug/100 uL dose of a particular BMP/matrix sample, for example BMP/PLGA porous particles/blood clot, as disclosed in U.S. Pat. No. 5,171,579, the disclosure of which is hereby incorporated by reference. After 14 days, the rats are sacrificed and each animal is evaluated for bone formation.

Example X

Polyclonal Antibodies Against the Truncated BMP Receptor

Three rabbits are injected with purified truncated BMP receptor protein. Polyclonal antibodies from sera of these rabbits are purified by chromatography on a Protein A column. The antibodies are tested for the ability to bind BMP receptors.

Example XI

Monoclonal Antibodies Against the Truncated Human BMP Receptor

Three sets of three mice are immunized with purified truncated BMP receptor protein. The spleens of the mice are used to generate multiple hybridoma cell lines. The conditioned media from non-clonal mouse hybridoma lines are tested for ability to bind to BMP receptors. Clonal lines can be developed from these by sequential serial and limiting dilution cloning. As non-clonal lines become clonal those lines which are positive for activity in the non-clonal stage will retain the ability to produce an antibody which binds BMP receptor. Conversely, lines which are negative will stay negative throughout the cloning process. Monoclonal antibodies may be purified from ascites derived from both positive and negative hybridoma clones.

What is claimed is:

1. An isolated DNA molecule comprising a DNA sequence encoding a serine/threonine kinase receptor protein, wherein the DNA sequence comprises nucleotides 474 to 2000 of SEQ ID NO: 5.

2. An isolated DNA molecule comprising a DNA sequence encoding a serine/threonine kinase receptor protein, wherein the DNA sequence comprises nucleotides encoding for amino acids 18 to 509 of SEQ ID NO: 6.

3. An isolated host cell transformed with the DNA molecule of claim 2.

4. An isolated DNA molecule comprising the DNA sequence of CFK1-10a.

* * * * *

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
        (A) LENGTH: 1813 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: CFK1-23a (ix) FEATURE:
        (A) NAME/KEY: CDS
        (B) LOCATION: 61..1656

(xi) SEQUENCE DESCRIPTION: SEQ ID NO: 1:

```
CTAGTGGATC CCCCGGGCTG CAGGAATTCT GCGGCCGCCA GGACACGTGC GAATTGGACA        60

ATG ACT CAG CTA TAC ACT TAC ATC AGA TTA CTG GGA GCC TGT CTG TTC        108
Met Thr Gln Leu Tyr Thr Tyr Ile Arg Leu Leu Gly Ala Cys Leu Phe
 1               5                  10                  15

ATC ATT TCT CAT GTT CAA GGG CAG AAT CTA GAT AGT ATG CTC CAT GGT        156
Ile Ile Ser His Val Gln Gly Gln Asn Leu Asp Ser Met Leu His Gly
                20                  25                  30

ACT GGT ATG AAA TCA GAC GTG GAC CAG AAG AAG CCG GAA AAT GGA GTG        204
Thr Gly Met Lys Ser Asp Val Asp Gln Lys Lys Pro Glu Asn Gly Val
            35                  40                  45

ACG TTA GCA CCA GAG GAC ACC TTA CCT TTC TTA AAA TGC TAT TGC TCA        252
Thr Leu Ala Pro Glu Asp Thr Leu Pro Phe Leu Lys Cys Tyr Cys Ser
        50                  55                  60

GGA CAC TGC CCA GAT GAC GCT ATT AAT AAC ACA TGC ATA ACT AAT GGC        300
Gly His Cys Pro Asp Asp Ala Ile Asn Asn Thr Cys Ile Thr Asn Gly
 65                  70                  75                  80

CAT TGC TTT GCC ATT ATA GAA GAA GAT GAT CAG GGA GAA ACC ACG TTA        348
His Cys Phe Ala Ile Ile Glu Glu Asp Asp Gln Gly Glu Thr Thr Leu
                85                  90                  95

ACT TCT GGG TGT ATG AAG TAT GAA GGC TCT GAT TTT CAA TGC AAG GAT        396
Thr Ser Gly Cys Met Lys Tyr Glu Gly Ser Asp Phe Gln Cys Lys Asp
            100                 105                 110
```

```
TCA CCA AAA GCC CAG CTA CGC AGG ACA ATA GAA TGT TGT CGG ACC AAT       444
Ser Pro Lys Ala Gln Leu Arg Arg Thr Ile Glu Cys Cys Arg Thr Asn
        115                 120                 125

TTG TGC AAC CAA TAT TTG CAG CCT ACA CTG CCC CCT GTC GTT ATA GGC       492
Leu Cys Asn Gln Tyr Leu Gln Pro Thr Leu Pro Pro Val Val Ile Gly
130                 135                 140

CCA TTC TTT GAT GGC AGC GTC CGA TGG CTG GCT GTG CTC ATC TCT ATG       540
Pro Phe Phe Asp Gly Ser Val Arg Trp Leu Ala Val Leu Ile Ser Met
145                 150                 155                 160

GCT GTC TGT ATT GTC GCC ATG ATC GTC TTC TCC AGC TGC TTC TGT TAC       588
Ala Val Cys Ile Val Ala Met Ile Val Phe Ser Ser Cys Phe Cys Tyr
            165                 170                 175

AAA CAT TAC TGT AAG AGT ATC TCA AGC AGA GGT CGT TAC AAC CGT GAC       636
Lys His Tyr Cys Lys Ser Ile Ser Ser Arg Gly Arg Tyr Asn Arg Asp
            180                 185                 190

TTG GAA CAG GAT GAA GCA TTT ATT CCA GTA GGA GAA TCA CTG AAA GAC       684
Leu Glu Gln Asp Glu Ala Phe Ile Pro Val Gly Glu Ser Leu Lys Asp
        195                 200                 205

CTG ATT GAC CAG TCA CAA AGC TCT GGT AGT GGA TCT GGA TTA CCT TTA       732
Leu Ile Asp Gln Ser Gln Ser Ser Gly Ser Gly Ser Gly Leu Pro Leu
210                 215                 220

TTG GTT CAG CGA ACT ATT GCC AAA CAG ATT CAG ATG GTT CGG CAG GTT       780
Leu Val Gln Arg Thr Ile Ala Lys Gln Ile Gln Met Val Arg Gln Val
225                 230                 235                 240

GGT AAG GGC CGG TAT GGA GAA GTA TGG ATG GGT AAA TGG CGT GGT GAA       828
Gly Lys Gly Arg Tyr Gly Glu Val Trp Met Gly Lys Trp Arg Gly Glu
            245                 250                 255

AAA GTG GCT GTC AAA GTA TTT TTT ACC ACT GAA GAA GCT AGC TGG TTT       876
Lys Val Ala Val Lys Val Phe Phe Thr Thr Glu Glu Ala Ser Trp Phe
            260                 265                 270

AGA GAA ACA GAA ATC TAC CAG ACG GTG TTA ATG CGT CAT GAA AAT ATA       924
Arg Glu Thr Glu Ile Tyr Gln Thr Val Leu Met Arg His Glu Asn Ile
        275                 280                 285

CTT GGT TTT ATA GCT GCA GAC ATT AAA GGC ACC GGT TCC TGG ACT CAG       972
Leu Gly Phe Ile Ala Ala Asp Ile Lys Gly Thr Gly Ser Trp Thr Gln
290                 295                 300

CTG TAT TTG ATT ACT GAT TAC CAT GAG AAT GGG TCT CTC TAT GAC TTC      1020
Leu Tyr Leu Ile Thr Asp Tyr His Glu Asn Gly Ser Leu Tyr Asp Phe
305                 310                 315                 320

CTG AAA TGT GCC ACC CTG GAC ACC AGA GCC CTA CTC AAG TTA GCT TAT      1068
Leu Lys Cys Ala Thr Leu Asp Thr Arg Ala Leu Leu Lys Leu Ala Tyr
            325                 330                 335

TCT GCT GCC TGT GGT CTG TGC CAC CTC CAC ACA GAA ATT TAT GGC ACG      1116
Ser Ala Ala Cys Gly Leu Cys His Leu His Thr Glu Ile Tyr Gly Thr
            340                 345                 350

CAA GGC AAG CCT GCA ATT GCT CAT CGA GAC CTG AAG AGC AAA AAC ATC      1164
Gln Gly Lys Pro Ala Ile Ala His Arg Asp Leu Lys Ser Lys Asn Ile
        355                 360                 365

CTT ATT AAG AAA AAT GGT AGT TGC TGT ATT GCT GAC CTG GGC CTA GCT      1212
Leu Ile Lys Lys Asn Gly Ser Cys Cys Ile Ala Asp Leu Gly Leu Ala
370                 375                 380

GTT AAA TTC AAC AGT GAC ACA AAT GAA GTT GAC ATA CCC TTG AAC ACC      1260
Val Lys Phe Asn Ser Asp Thr Asn Glu Val Asp Ile Pro Leu Asn Thr
385                 390                 395                 400

AGG GTG GGC ACC AGG CGG TAC ATG GCT CCA GAA GTG CTG GAC GAG AGC      1308
Arg Val Gly Thr Arg Arg Tyr Met Ala Pro Glu Val Leu Asp Glu Ser
            405                 410                 415

CTG AGT AAA AAC CAT TTC CAG CCC TAC ATC ATG GCT GAC ATC TAC AGC      1356
Leu Ser Lys Asn His Phe Gln Pro Tyr Ile Met Ala Asp Ile Tyr Ser
            420                 425                 430
```

```
TTT GGT TTG ATC ATT TGG GAG ATG GCC CGT CGC TGT ATT ACA GGA GGA         1404
Phe Gly Leu Ile Ile Trp Glu Met Ala Arg Arg Cys Ile Thr Gly Gly
        435                 440                 445

ATC GTG GAG GAA TAT CAA TTA CCA TAT TAC AAC ATG GTG CCT AGT GAC         1452
Ile Val Glu Glu Tyr Gln Leu Pro Tyr Tyr Asn Met Val Pro Ser Asp
    450                 455                 460

CCA TCT TAT GAA GAC ATG CGT GAG GTC GTG TGT GTG AAA CGC TTG CGG         1500
Pro Ser Tyr Glu Asp Met Arg Glu Val Val Cys Val Lys Arg Leu Arg
465                 470                 475                 480

CCA ATC GTC TCT AAC CGC TGG AAC AGT GAT GAA TGT CTT CGA GCC GTT         1548
Pro Ile Val Ser Asn Arg Trp Asn Ser Asp Glu Cys Leu Arg Ala Val
                485                 490                 495

TTG AAG CTG ATG TCA GAA TGC TGG GCC CAT AAT CCA GCA TCC AGA CTC         1596
Leu Lys Leu Met Ser Glu Cys Trp Ala His Asn Pro Ala Ser Arg Leu
            500                 505                 510

ACA GCT TTG AGA ATC AAG AAG ACG CTC GCA AAG ATG GTT GAA TCC CAG         1644
Thr Ala Leu Arg Ile Lys Lys Thr Leu Ala Lys Met Val Glu Ser Gln
        515                 520                 525

GAT GTA AAG ATT TGACAAACAG TTTTGAGAAA GAATTTAGAC TGCAAGAAAT             1696
Asp Val Lys Ile
    530

TCACCCGAGG AAGGGTGGAG TTAGCATGGA CTAGGATGTC GGCTTGGTTT CCAGACTCTC       1756

TCCTCTACCA TCTTCACAGG CTGCTAACAG TAAACCTTTC AGGACTCTGC AGAATGC          1813

(2) INFORMATION FOR SEQ ID NO: 2:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO: 2:

Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
            20                  25                  30

Thr Gly Met Lys Ser Asp Val Asp Gln Lys Lys Pro Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Val Arg Trp Leu Ala Val Leu Ile Ser Met
145                 150                 155                 160

Ala Val Cys Ile Val Ala Met Ile Val Phe Ser Ser Cys Phe Cys Tyr
                165                 170                 175

Lys His Tyr Cys Lys Ser Ile Ser Ser Arg Gly Arg Tyr Asn Arg Asp
```

```
                180                 185                 190
Leu Glu Gln Asp Glu Ala Phe Ile Pro Val Gly Glu Ser Leu Lys Asp
            195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
    370                 375                 380

Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
                405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
530

(2) INFORMATION FOR SEQ ID NO: 3:

(i) SEQUENCE CHARACTERISTICS:
        (A) LENGTH: 2076 base pairs
        (B) TYPE: nucleic acid
        (C) STRANDEDNESS: single
        (D) TOPOLOGY: linear (ii) MOLECULE TYPE: DNA (genomic)
```

```
       (vii) IMMEDIATE SOURCE:
             (B) CLONE: CFK1-43a (ix) FEATURE:
             (A) NAME/KEY: CDS
             (B) LOCATION: 247..1752

(xi) SEQUENCE DESCRIPTION: SEQ ID NO: 3:

GCGGCCGCGC CGGCGTGGTG CTCGGAGTGC GGGCGCCGAG GACCCGGGAC CAGGGGCGCG      60

GCGGCGGGTT GGAGTTCAAG GTACTCGTTA CGTGTGACGA GGAAGTGAAG CCCATTCCAT     120

GCCTTGCTGA GAAAGGTTCA AACTTCGGCT GAATCACAAC CATTTGGCGC TGAGCTATGA     180

CAAGAGAGCA AACAAAAAGT TAAAGGAGCA ACTCGGCCAT AAGTGACAGA GAAGTTCGTT     240

GATAAC ATG CTC TTA CGA AGC TCT GGA AAA TTA AAT GTG GGC ACC AAG        288
       Met Leu Leu Arg Ser Ser Gly Lys Leu Asn Val Gly Thr Lys
         1               5                  10

AAG GAG GAT GGT GAG AGT ACA GCC CCC ACT GCT CGG CCC AAG GTC CTG       336
Lys Glu Asp Gly Glu Ser Thr Ala Pro Thr Ala Arg Pro Lys Val Leu
 15                  20                  25                  30

CGT TGT AAA TGC CAC CAC CAC TGT CCT GAA GAC TCA GTC AAC AAT ATC       384
Arg Cys Lys Cys His His His Cys Pro Glu Asp Ser Val Asn Asn Ile
                     35                  40                  45

TGC AGC ACA GAT GGG TAC TGC TTC ACG ATG ATA GAA GAA GAC GAC TCT       432
Cys Ser Thr Asp Gly Tyr Cys Phe Thr Met Ile Glu Glu Asp Asp Ser
                 50                  55                  60

GGA ACG CCT GTT GTC ACC TCC GGA TGC TTA GGA CTA GAA GGG TCA GAT       480
Gly Thr Pro Val Val Thr Ser Gly Cys Leu Gly Leu Glu Gly Ser Asp
             65                  70                  75

TTT CAA TGT CGC GAC ACG CCC ATC CCT CAT CAG AGA AGG TCA ATT GAA       528
Phe Gln Cys Arg Asp Thr Pro Ile Pro His Gln Arg Arg Ser Ile Glu
         80                  85                  90

TGC TGC ACA GAA AGG AAC GAA TGT AAT AAA GAT CTC CAC CCC ACG CTG       576
Cys Cys Thr Glu Arg Asn Glu Cys Asn Lys Asp Leu His Pro Thr Leu
 95                 100                 105                 110

CCT CCC CTG AAG GAC AGA GAT TTT GTT GAT GGA CCC ATA CAC CAC AAA       624
Pro Pro Leu Lys Asp Arg Asp Phe Val Asp Gly Pro Ile His His Lys
                115                 120                 125

GCC TTA CTC ATA TCT GTG ACT GTC TGT AGT TTA CTC TTG GTC CTC ATT       672
Ala Leu Leu Ile Ser Val Thr Val Cys Ser Leu Leu Leu Val Leu Ile
            130                 135                 140

ATT TTA TTC TGT TAC TTC AGG TAT AAA AGA CAA GAA GCC AGA CCT CGG       720
Ile Leu Phe Cys Tyr Phe Arg Tyr Lys Arg Gln Glu Ala Arg Pro Arg
        145                 150                 155

TAC AGC ATT GGG CTG GAG CAG GAT GAA ACG TAC ATT CCT CCT GGA GAA       768
Tyr Ser Ile Gly Leu Glu Gln Asp Glu Thr Tyr Ile Pro Pro Gly Glu
    160                 165                 170

TCC CTG AGA GAC TTG ATT GAG CAA TCG CAG AGC TCG GGA AGT GGC TCA       816
Ser Leu Arg Asp Leu Ile Glu Gln Ser Gln Ser Ser Gly Ser Gly Ser
175                 180                 185                 190

GGA CTC CCT CTG CTG GTC CAA AGG ACA ATA GCT AAG CAA ATT CAG ATG       864
Gly Leu Pro Leu Leu Val Gln Arg Thr Ile Ala Lys Gln Ile Gln Met
                195                 200                 205

GTG AAG CAA ATT GGA AAA GGT CGC TAT GGC GAA GTG TGG ATG GGA AAG       912
Val Lys Gln Ile Gly Lys Gly Arg Tyr Gly Glu Val Trp Met Gly Lys
            210                 215                 220

TGG CGT GGA GAA AAG GTA GCT GTG AAA GTG TTC TTC ACC ACG GAG GAA       960
Trp Arg Gly Glu Lys Val Ala Val Lys Val Phe Phe Thr Thr Glu Glu
        225                 230                 235

GCC AGC TGG TTC CGA GAG ACT GAG ATA TAT CAG ACG GTC CTG ATG AGG      1008
Ala Ser Trp Phe Arg Glu Thr Glu Ile Tyr Gln Thr Val Leu Met Arg
```

```
            240                 245                 250
CAC GAG AAC ATT CTG GGG TTC ATT GCA GCA GAT ATC AAA GGG ACT GGG       1056
His Glu Asn Ile Leu Gly Phe Ile Ala Ala Asp Ile Lys Gly Thr Gly
255                 260                 265                 270

TCT TGG ACT CAG TTA TAC CTC ATC ACA GAC TAT CAT GAA AAC GGG TCT       1104
Ser Trp Thr Gln Leu Tyr Leu Ile Thr Asp Tyr His Glu Asn Gly Ser
                    275                 280                 285

CTT TAT GAC TAT CTG AAA TCC ACC ACC TTA GAT GCC AAG TCC ATG CTG       1152
Leu Tyr Asp Tyr Leu Lys Ser Thr Thr Leu Asp Ala Lys Ser Met Leu
                290                 295                 300

AAG CTA GCC TAC TCG TCT GTC AGC GGC CTG TGC CAT CTA CAC ACG GAA       1200
Lys Leu Ala Tyr Ser Ser Val Ser Gly Leu Cys His Leu His Thr Glu
            305                 310                 315

ATC TTC AGC ACT CAA GGC AAG CCA GCC ATT GCC CAT CGG GAC TTG AAA       1248
Ile Phe Ser Thr Gln Gly Lys Pro Ala Ile Ala His Arg Asp Leu Lys
        320                 325                 330

AGT AAA AAC ATC CTG GTG AAG AAA AAT GGA ACT TGC TGC ATA GCA GAC       1296
Ser Lys Asn Ile Leu Val Lys Lys Asn Gly Thr Cys Cys Ile Ala Asp
335                 340                 345                 350

CTG GGC CTG GCT GTC AAG TTC ATT AGT GAC ACA AAT GAG GTT GAC ATT       1344
Leu Gly Leu Ala Val Lys Phe Ile Ser Asp Thr Asn Glu Val Asp Ile
                355                 360                 365

CCA CCC AAC ACC CGG GTT GGC ACC AAG CGC TAT ATG CCT CCA GAA GTG       1392
Pro Pro Asn Thr Arg Val Gly Thr Lys Arg Tyr Met Pro Pro Glu Val
                370                 375                 380

CTG GAC GAG AGC TTG AAT AGA ACT CAT TTC CAG TCC TAC ATC ATG GCT       1440
Leu Asp Glu Ser Leu Asn Arg Thr His Phe Gln Ser Tyr Ile Met Ala
            385                 390                 395

GAC ATG TAC AGC TTT GGA CTC ATC CTC TGG GAG ATT GCA AGG AGA TGT       1488
Asp Met Tyr Ser Phe Gly Leu Ile Leu Trp Glu Ile Ala Arg Arg Cys
        400                 405                 410

GTT TCT GGA GGT ATA GTG GAA GAA TAC CAG CTT CCA TAT CAC GAC CTG       1536
Val Ser Gly Gly Ile Val Glu Glu Tyr Gln Leu Pro Tyr His Asp Leu
415                 420                 425                 430

GTG CCC AGT GAC CCC TCT TAT GAG GAC ATG AGA GAA ATT GTG TGT ATG       1584
Val Pro Ser Asp Pro Ser Tyr Glu Asp Met Arg Glu Ile Val Cys Met
                435                 440                 445

AAG AAG TTA CGG CCT TCA TTC CCC AAT CGA TGG AGC AGT GAC GAG TGC       1632
Lys Lys Leu Arg Pro Ser Phe Pro Asn Arg Trp Ser Ser Asp Glu Cys
                450                 455                 460

CTC AGG CAA ATG GGG AAG CTT ATG ACA GAG TGC TGG GCG CAT AAT CCT       1680
Leu Arg Gln Met Gly Lys Leu Met Thr Glu Cys Trp Ala His Asn Pro
            465                 470                 475

GCC TCC AGG CTG ACG GCC CTG AGA GTT AAG AAA ACA CTT GCC AAA ATG       1728
Ala Ser Arg Leu Thr Ala Leu Arg Val Lys Lys Thr Leu Ala Lys Met
        480                 485                 490

TCA GAG TCC CAG GAC ATT AAA CTC TGACGTCAGG TACTTGTGGA CAGAGCAAGG     1782
Ser Glu Ser Gln Asp Ile Lys Leu
495                 500

AATTACACAG AAGCATCCTT AGCCCAAGCC TTGAACGTTG ATCTACTGCC CAGTGAGTTC    1842

AGACTTTCCT CTAAGAGAGC AAGCTGGACA GACACAGAGG AACCCAGAAA CACGGCTTCA    1902

CCATGGCTTT CTGAGGAGGG GAAACCATTT GGGTAACTTG TTCAAGATAT GATGCATGTT    1962

GCTTTCTAAG AAAGCCCTGT ATTTTGGGAT TACCATTTTT TTTAAAGAAG AAAGATACTT    2022

TAATTTTTAC CAAAATAAAA CAAATATTAT AGAAAAAAAG CGGCCGCAGA ATTC          2076

(2) INFORMATION FOR SEQ ID NO: 4:
```

(i) SEQUENCE CHARACTERISTICS:
    (A) LENGTH: 502 amino acids
    (B) TYPE: amino acid
    (D) TOPOLOGY: linear (ii) MOLECULE TYPE: protein (xi) SEQUENCE DESCRIPTION: SEQ ID NO: 4:

```
Met Leu Leu Arg Ser Ser Gly Lys Leu Asn Val Gly Thr Lys Lys Glu
 1               5                  10                  15

Asp Gly Glu Ser Thr Ala Pro Thr Ala Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Thr
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asp Arg Asp Phe Val Asp Gly Pro Ile His His Lys Ala Leu
        115                 120                 125

Leu Ile Ser Val Thr Val Cys Ser Leu Leu Val Leu Ile Ile Leu
130                 135                 140

Phe Cys Tyr Phe Arg Tyr Lys Arg Gln Glu Ala Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
```

-continued

```
            370                 375                 380
Glu Ser Leu Asn Arg Thr His Phe Gln Ser Tyr Ile Met Ala Asp Met
385                 390                 395                 400

Tyr Ser Phe Gly Leu Ile Leu Trp Glu Ile Ala Arg Arg Cys Val Ser
                405                 410                 415

Gly Gly Ile Val Glu Glu Tyr Gln Leu Pro Tyr His Asp Leu Val Pro
                420                 425                 430

Ser Asp Pro Ser Tyr Glu Asp Met Arg Glu Ile Val Cys Met Lys Lys
                435                 440                 445

Leu Arg Pro Ser Phe Pro Asn Arg Trp Ser Ser Asp Glu Cys Leu Arg
                450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
                500
```

(2) INFORMATION FOR SEQ ID NO: 5:

(i) SEQUENCE CHARACTERISTICS:
        (A) LENGTH: 3238 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: CFK1-10a (ix) FEATURE:
        (A) NAME/KEY: CDS
        (B) LOCATION: 474..2000

(xi) SEQUENCE DESCRIPTION: SEQ ID NO: 5:

```
GAATTCTGCG GCCGCGAGGC TGCATTAAGT GGGATATGCC ACCCGTGATT CTGACAGCCG      60

TGACTGCGTG GAGCCTGCTC CGGAACTCTC CACAGAGGAG CAAAGGAGCT GCCCTCTGTG     120

TCTCCCCGCC CTTCAGCGAG AGTCTGGAAA GAGAACCGAG GTGCTACTGC AGTGGATGAG     180

TAGAGAAGAG TCTGCATCCA GTGCTGGTGA GCTTGTCTGG CTATAGGGAG CCTGCTGGGG     240

GAAACTTACA GCTTCAGAAG ACTCCTGGAG AGCCTCTCCC TCCACACTCT CCCTTTGAGC     300

AGTCAGTGCC TCTCTGCTGG AGAACCTGTG CTGGGTGTGC CCAGAGCTG ACTTTGACTG      360

TAGCCTGTCA GGCTCTCCCT GGACCTCACG GAACAGCATT GCCAGCCACA CGGCTTCCAA     420

CAAATCACCT CTTTTCATGC TGTTTGGCAC AGATCGAATC TACAGGTTAT ACA ATG        476
                                                        Met
                                                          1

GTC GAT GGA GCA ATG ATC CTT TCT GTG CTA ATG ATG ATG GCT CTC CCT      524
Val Asp Gly Ala Met Ile Leu Ser Val Leu Met Met Met Ala Leu Pro
             5                   10                  15

TCC CCG AGT ATG GAA GAT GAG GAG CCC AAG GTC AAC CCG AAG CTT TAC      572
Ser Pro Ser Met Glu Asp Glu Glu Pro Lys Val Asn Pro Lys Leu Tyr
            20                  25                  30

ATG TGT GTG TGT GAG GGC CTC TCC TGC GGG AAC GAG GAC CAC TGT GAG      620
Met Cys Val Cys Glu Gly Leu Ser Cys Gly Asn Glu Asp His Cys Glu
        35                  40                  45

GGC CAG CAG TGT TTT TCC TCC CTG AGC GTC AAT GAT GGC TTC CGC GTC      668
Gly Gln Gln Cys Phe Ser Ser Leu Ser Val Asn Asp Gly Phe Arg Val
50                  55                  60                  65
```

```
TAC CAG AAG GGC TGC TTT CAG GTC TAT GAG CAG GGG AAG ATG ACG TGT          716
Tyr Gln Lys Gly Cys Phe Gln Val Tyr Glu Gln Gly Lys Met Thr Cys
            70                  75                  80

AAG ACC CCG CCG TCG CCT GGC CAG GCT GTG GAG TGC TGC CAA GGG GAC          764
Lys Thr Pro Pro Ser Pro Gly Gln Ala Val Glu Cys Cys Gln Gly Asp
                85                  90                  95

TGG TGC AAC AGG AAC GTC ACG GCC CGG CTG CCC ACT AAA GGG AAA TCC          812
Trp Cys Asn Arg Asn Val Thr Ala Arg Leu Pro Thr Lys Gly Lys Ser
            100                 105                 110

TTC CCT GGA TCG CAG AAC TTC CAC CTG GAA GTT GGC CTT ATC ATC CTC          860
Phe Pro Gly Ser Gln Asn Phe His Leu Glu Val Gly Leu Ile Ile Leu
        115                 120                 125

TCC GTG GTG TTT GCG GTA TGC CTT TTC GCT TGC ATC CTT GGC GTT GCT          908
Ser Val Val Phe Ala Val Cys Leu Phe Ala Cys Ile Leu Gly Val Ala
130                 135                 140                 145

CTC AGG AAG TTT AAA AGG CGC AAT CAA GAG CGC CTG AAC CCC AGA GAC          956
Leu Arg Lys Phe Lys Arg Arg Asn Gln Glu Arg Leu Asn Pro Arg Asp
                150                 155                 160

GTG GAG TAC GGT ACT ATC GAA GGG CTC ATC ACC ACC AAC GTC GGA GAT         1004
Val Glu Tyr Gly Thr Ile Glu Gly Leu Ile Thr Thr Asn Val Gly Asp
            165                 170                 175

AGC ACT CTA GCG GAA TTA CTA GAT CAC TCA TGT ACA TCA GGA AGT GGC         1052
Ser Thr Leu Ala Glu Leu Leu Asp His Ser Cys Thr Ser Gly Ser Gly
        180                 185                 190

TCC GGT CTT CCT TTT CTG GTA CAG AGA ACT GTG GCT CGA CAG ATA ACC         1100
Ser Gly Leu Pro Phe Leu Val Gln Arg Thr Val Ala Arg Gln Ile Thr
        195                 200                 205

CTG TTG GAG TGT GTC GGG AAG GGC CGG TAT GGA GAA GTG TGG AGG GGC         1148
Leu Leu Glu Cys Val Gly Lys Gly Arg Tyr Gly Glu Val Trp Arg Gly
210                 215                 220                 225

AGC TGG CAA GGC GAA AAT GTT GCT GTG AAG ATC TTC TCC TCC CGT GAT         1196
Ser Trp Gln Gly Glu Asn Val Ala Val Lys Ile Phe Ser Ser Arg Asp
                230                 235                 240

GAG AAG TCG TGG TTC AGG GAG ACA GAA TTG TAC AAC ACG GTG ATG CTG         1244
Glu Lys Ser Trp Phe Arg Glu Thr Glu Leu Tyr Asn Thr Val Met Leu
            245                 250                 255

AGG CAT GAG AAT ATC TTA GGT TTC ATT GCT TCA GAC ATG ACC TCT AGA         1292
Arg His Glu Asn Ile Leu Gly Phe Ile Ala Ser Asp Met Thr Ser Arg
        260                 265                 270

CAC TCC AGT ACC CAG CTG TGG CTC ATT ACA CAT TAC CAC GAA ATG GGA         1340
His Ser Ser Thr Gln Leu Trp Leu Ile Thr His Tyr His Glu Met Gly
        275                 280                 285

TCG TTG TAT GAC TAC CTT CAG CTC ACC ACT CTG GAC ACC GTT AGC TGC         1388
Ser Leu Tyr Asp Tyr Leu Gln Leu Thr Thr Leu Asp Thr Val Ser Cys
290                 295                 300                 305

CTT CGG ATC GTG TTG TCC ATA GCC AGC GGC CTT GCA CAC TTG CAC ATA         1436
Leu Arg Ile Val Leu Ser Ile Ala Ser Gly Leu Ala His Leu His Ile
                310                 315                 320

GAG ATA TTT GGG ACC CAG GGG AAG TCT GCC ATC GCC CAC CGA GAT CTA         1484
Glu Ile Phe Gly Thr Gln Gly Lys Ser Ala Ile Ala His Arg Asp Leu
            325                 330                 335

AAG AGC AAA AAC ATC CTC GTG AAG AAG AAC GGA CAG TGC TGC ATA GCA         1532
Lys Ser Lys Asn Ile Leu Val Lys Lys Asn Gly Gln Cys Cys Ile Ala
        340                 345                 350

GAT TTG GGC CTG GCA GTC ATG CAT TCC CAG AGC ACG AAT CAG CTT GAT         1580
Asp Leu Gly Leu Ala Val Met His Ser Gln Ser Thr Asn Gln Leu Asp
355                 360                 365

GTG GGA AAC AAC CCC CGT GTG GGG ACC AAG CGC TAC ATG GCC CCT GAA         1628
Val Gly Asn Asn Pro Arg Val Gly Thr Lys Arg Tyr Met Ala Pro Glu
```

```
 370                 375                 380                 385
GTG CTT GAT GAA ACC ATC CAA GTG GAT TGC TTT GAT TCT TAT AAG AGG        1676
Val Leu Asp Glu Thr Ile Gln Val Asp Cys Phe Asp Ser Tyr Lys Arg
                390                 395                 400

GTC GAT ATT TGG GCC TTT GGC CTC GTT CTG TGG GAA GTG GCC AGG AGG        1724
Val Asp Ile Trp Ala Phe Gly Leu Val Leu Trp Glu Val Ala Arg Arg
                405                 410                 415

ATG GTG AGC AAT GGT ATA GTG GAA GAT TAC AAG CCA CCA TTC TAT GAT        1772
Met Val Ser Asn Gly Ile Val Glu Asp Tyr Lys Pro Pro Phe Tyr Asp
                420                 425                 430

GTT GTT CCC AAT GAC CCA AGT TTT GAA GAT ATG AGG AAA GTT GTC TGT        1820
Val Val Pro Asn Asp Pro Ser Phe Glu Asp Met Arg Lys Val Val Cys
                435                 440                 445

GTG GAT CAA CAG AGG CCA AAC ATA CCT AAC AGA TGG TTC TCA GAC CCG        1868
Val Asp Gln Gln Arg Pro Asn Ile Pro Asn Arg Trp Phe Ser Asp Pro
450                 455                 460                 465

ACA TTA ACT TCT CTG GCG AAG CTG ATG AAA GAA TGC TGG TAC CAG AAC        1916
Thr Leu Thr Ser Leu Ala Lys Leu Met Lys Glu Cys Trp Tyr Gln Asn
                470                 475                 480

CCA TCC GCC AGA CTC ACA GCT CTA CGT ATC AAA AAG ACT TTG ACC AAA        1964
Pro Ser Ala Arg Leu Thr Ala Leu Arg Ile Lys Lys Thr Leu Thr Lys
                485                 490                 495

ATT GAT AAC TCC CTA GAC AAA TTA AAA ACT GAC TGT TGACATTGTC             2010
Ile Asp Asn Ser Leu Asp Lys Leu Lys Thr Asp Cys
                500                 505

ACCGGTGTCA AGAAGGAGAG TCAATGCTGT CATTGTCCAG CTGGGACCTA ATGCTGGCCT      2070

GACTGGTTGT CAGAACAGAA TCCATCTGTC CCCCTCTCCC CCCAACTCCC GAAGTGGCTG      2130

CTTTGACAAA AGCAGATGTC TCTTCCCAGC CATGTTCCGG GGGAGACACC AAAACCACCC      2190

TAACCTCGCT CAGAAACTGT GACTCGAGCA CTTGATGAAC TGTTCACACC GCAAAGACTA      2250

ACGGTGGGCA GGTATGTTTG CAAGGGGGAG GGAAGTGGAG GAGCACAGAG AGATCCTGCA      2310

GGAGATCTGG GCATTAGGAC AGTGGCTCTT TGCGTATCTT CCACGGGTCT CCTAGACTCG      2370

CCCCACGGGA AACTCAAGGA GGCGGTGAAT TCGTAATCAG CAATATTGGC TGCGCCTACT      2430

CTTCTCTGTT GCACTAGGAA TTCTCTGCAT TCCTTACTTG CACTGTCGTC CTTAATCTTA      2490

AAGACCCGAC TTGCCAAAAC ATTGGCTGCC TACTTCACTG GCCTGTCTCT GGACAATAGG      2550

AATTCAATCT GGCGAAACAA AAATGTAATG TTGGACTTTG CTGCATTTTA CACACGTGCC      2610

GATGTTTACA ACGATGCAAA CATTAGGAAT TGTTTAGACA CAACTTTGCA AATTATTTAT      2670

TACTGGTGCA CTTAGCAGTT TTTGTTTTTT TTTGTTTTTT TGTTTTTTTT TTGTTTTGTT      2730

TTGTTTTTAT ATATAAAACT GCCTCGTGCG TATGTTAAAG CTTATTTTTA TGTGGTCTTA      2790

TGATTTATT ACCGAAATGT TTTTAACACC CGATTCTGAA ATGGATGTTT TCTTTTATTA       2850

TCAGTTAAAT TCACATTTTA AATGCTTCAC TTTTTTTTTA TGTGTGTAGA CTGTAACTTT      2910

CTTTTCAGTT AGTATACAGA ACGTATTTAG CCATTACCCA TGCAACACCA CCCAATATAT      2970

TACTGATTTA GAAGCAAAGA TTTCAGTAGA ATTTAGTCC CAAACGCTGT GGGGGGGAAA       3030

TGCATCTTCT TCGGAACTAT CCATTACATG CATTTAAACT CTGCCAGAAA AAAAAATAAC      3090

TATTTTGTTT TAATCTACTT TTTGTATTTA GTAGTTATTT GTATAAATTA AATAAACTGT      3150

TTTCAAGTCA AAAAAAAAAA AAAAAAAAA  AAAAAAAAAA AAAAAAAAAA AAAAAAAAAT      3210

AAAAAAAAAA AAAGCGGCCG CAGAATTC                                         3238

(2) INFORMATION FOR SEQ ID NO: 6:
```

-continued (i) SEQUENCE CHARACTERISTICS:
    (A) LENGTH: 509 amino acids
    (B) TYPE: amino acid
    (D) TOPOLOGY: linear (ii) MOLECULE TYPE: protein (xi) SEQUENCE DESCRIPTION: SEQ ID NO: 6:

```
Met Val Asp Gly Ala Met Ile Leu Ser Val Leu Met Met Ala Leu
 1               5                  10                  15

Pro Ser Pro Ser Met Glu Asp Glu Pro Lys Val Asn Pro Lys Leu
                20                  25                  30

Tyr Met Cys Val Cys Glu Gly Leu Ser Cys Gly Asn Glu Asp His Cys
            35                  40                  45

Glu Gly Gln Gln Cys Phe Ser Ser Leu Ser Val Asn Asp Gly Phe Arg
    50                  55                  60

Val Tyr Gln Lys Gly Cys Phe Gln Val Tyr Glu Gln Gly Lys Met Thr
 65                  70                  75                  80

Cys Lys Thr Pro Pro Ser Pro Gly Gln Ala Val Glu Cys Cys Gln Gly
                85                  90                  95

Asp Trp Cys Asn Arg Asn Val Thr Ala Arg Leu Pro Thr Lys Gly Lys
                100                 105                 110

Ser Phe Pro Gly Ser Gln Asn Phe His Leu Glu Val Gly Leu Ile Ile
            115                 120                 125

Leu Ser Val Val Phe Ala Val Cys Leu Phe Ala Cys Ile Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Glu Leu Leu Asp His Ser Cys Thr Ser Gly Ser
            180                 185                 190

Gly Ser Gly Leu Pro Phe Leu Val Gln Arg Thr Val Ala Arg Gln Ile
    195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Ser Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
    355                 360                 365

Asp Val Gly Asn Asn Pro Arg Val Gly Thr Lys Arg Tyr Met Ala Pro
```

```
                370                 375                 380
Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
                435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```

(2) INFORMATION FOR SEQ ID NO: 7:

(i) SEQUENCE CHARACTERISTICS:
        (A) LENGTH: 1647 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: W-101

(ix) FEATURE:
        (A) NAME/KEY: CDS
        (B) LOCATION: 80..1594

(xi) SEQUENCE DESCRIPTION: SEQ ID NO: 7:

```
GAATCTGCGG CCGCGAGGGA GAGAGGCGCC GGGGGCGCGC GCGCGCGCTG GGCGCTGCTG        60

GGCTGCGGCG GCGGTTACT ATG GCG GAG TCG GCC GGA GCC TCC TCC TTC TTC       112
                    Met Ala Glu Ser Ala Gly Ala Ser Ser Phe Phe
                     1               5                      10

CCC CTT GTT GTC CTC CTG CTC GCC GGC AGC GGC GGG TCC GGG CCC CGG        160
Pro Leu Val Val Leu Leu Leu Ala Gly Ser Gly Gly Ser Gly Pro Arg
            15                  20                  25

GGG ATC CAG GCT CTG CTG TGT GCG TGC ACC AGC TGC CTA CAG ACC AAC        208
Gly Ile Gln Ala Leu Leu Cys Ala Cys Thr Ser Cys Leu Gln Thr Asn
        30                  35                  40

TAC ACC TGT GAG ACA GAT GGG GCT TGC ATG GTC TCC ATC TTT AAC CTG        256
Tyr Thr Cys Glu Thr Asp Gly Ala Cys Met Val Ser Ile Phe Asn Leu
    45                  50                  55

GAT GGC GTG GAG CAC CAT GTA CGT ACC TGC ATC CCC AAG GTG GAG CTG        304
Asp Gly Val Glu His His Val Arg Thr Cys Ile Pro Lys Val Glu Leu
60                  65                  70                  75

GTT CCT GCT GGA AAG CCC TTC TAC TGC CTG AGT TCA GAG GAT CTG CGC        352
Val Pro Ala Gly Lys Pro Phe Tyr Cys Leu Ser Ser Glu Asp Leu Arg
            80                  85                  90

AAC ACA CAC TGC TGC TAT ATT GAC TTC TGC AAC AAG ATT GAC CTC AGG        400
Asn Thr His Cys Cys Tyr Ile Asp Phe Cys Asn Lys Ile Asp Leu Arg
        95                  100                 105

GTC CCC AGC GGA CAC CTC AAG GAG CCT GCG CAC CCC TCC ATG TGG GGC        448
Val Pro Ser Gly His Leu Lys Glu Pro Ala His Pro Ser Met Trp Gly
    110                 115                 120
```

```
CCT GTG GAG CTG GTC GGC ATC ATC GCC GGC CCC GTC TTC CTC CTC TTC    496
Pro Val Glu Leu Val Gly Ile Ile Ala Gly Pro Val Phe Leu Leu Phe
    125                 130                 135

CTT ATC ATT ATC ATC GTC TTC CTG GTC ATC AAC TAT CAC CAG CGT GTC    544
Leu Ile Ile Ile Ile Val Phe Leu Val Ile Asn Tyr His Gln Arg Val
140                 145                 150                 155

TAC CAT AAC CGC CAG AGG TTG GAC ATG GAG GAC CCC TCT TGC GAG ATG    592
Tyr His Asn Arg Gln Arg Leu Asp Met Glu Asp Pro Ser Cys Glu Met
                160                 165                 170

TGT CTC TCC AAA GAC AAG ACG CTC CAG GAT CTC GTC TAC GAC CTC TCC    640
Cys Leu Ser Lys Asp Lys Thr Leu Gln Asp Leu Val Tyr Asp Leu Ser
            175                 180                 185

ACG TCA GGG TCT GGC TCA GGG TTA CCC CTT TTT GTC CAG CGC ACA GTG    688
Thr Ser Gly Ser Gly Ser Gly Leu Pro Leu Phe Val Gln Arg Thr Val
        190                 195                 200

GCC CGA ACC ATT GTT TTA CAA GAG ATT ATC GGC AAG GGC CGG TTC GGG    736
Ala Arg Thr Ile Val Leu Gln Glu Ile Ile Gly Lys Gly Arg Phe Gly
    205                 210                 215

GAA GTA TGG CGT GGT CGC TGG AGG GGT GGT GAC GTG GCT GTG AAA ATC    784
Glu Val Trp Arg Gly Arg Trp Arg Gly Gly Asp Val Ala Val Lys Ile
220                 225                 230                 235

TTC TCT TCT CGT GAA GAA CGG TCT TGG TTC CGT GAA GCA GAG ATC TAC    832
Phe Ser Ser Arg Glu Glu Arg Ser Trp Phe Arg Glu Ala Glu Ile Tyr
                240                 245                 250

CAG ACC GTC ATG CTG CGC CAT GAA AAC ATC CTT GGC TTT ATT GCT GCT    880
Gln Thr Val Met Leu Arg His Glu Asn Ile Leu Gly Phe Ile Ala Ala
            255                 260                 265

GAC AAT AAA GAT AAT GGC ACC TGG ACC CAG CTG TGG CTT GTC TCT GAC    928
Asp Asn Lys Asp Asn Gly Thr Trp Thr Gln Leu Trp Leu Val Ser Asp
        270                 275                 280

TAT CAC GAG CAT GGC TCA CTG TTT GAT TAT CTG AAC CGC TAC ACC GTG    976
Tyr His Glu His Gly Ser Leu Phe Asp Tyr Leu Asn Arg Tyr Thr Val
    285                 290                 295

ACC ATT GAG GGC ATG ATT AAG CTA GCC TTG TCT GCA GCC AGT GGT TTG    1024
Thr Ile Glu Gly Met Ile Lys Leu Ala Leu Ser Ala Ala Ser Gly Leu
300                 305                 310                 315

GCA CAC CTG CAT ATG GAG ATT GTG GGC ACT CAA GGG AAG CCG GGA ATT    1072
Ala His Leu His Met Glu Ile Val Gly Thr Gln Gly Lys Pro Gly Ile
                320                 325                 330

GCT CAT CGA GAC TTG AAG TCA AAG AAC ATC CTG GTG AAA AAA AAT GGC    1120
Ala His Arg Asp Leu Lys Ser Lys Asn Ile Leu Val Lys Lys Asn Gly
            335                 340                 345

ATG TGT GCC ATT GCA GAC CTG GGC CTG GCT GTC CGT CAT GAT GCG GTC    1168
Met Cys Ala Ile Ala Asp Leu Gly Leu Ala Val Arg His Asp Ala Val
        350                 355                 360

ACT GAC ACC ATA GAC ATT GCT CCA AAT CAG AGG GTG GGG ACC AAA CGA    1216
Thr Asp Thr Ile Asp Ile Ala Pro Asn Gln Arg Val Gly Thr Lys Arg
    365                 370                 375

TAC ATG GCT CCT GAA GTC CTT GAC GAG ACA ATC AAC ATG AAG CAC TTT    1264
Tyr Met Ala Pro Glu Val Leu Asp Glu Thr Ile Asn Met Lys His Phe
380                 385                 390                 395

GAC TCC TTC AAA TGT GCC GAC ATC TAT GCC CTC GGG CTT GTC TAC TGG    1312
Asp Ser Phe Lys Cys Ala Asp Ile Tyr Ala Leu Gly Leu Val Tyr Trp
                400                 405                 410

GAG ATT GCA CGA AGA TGC AAT TCT GGA GGA GTC CAT GAA GAC TAT CAA    1360
Glu Ile Ala Arg Arg Cys Asn Ser Gly Gly Val His Glu Asp Tyr Gln
            415                 420                 425

CTG CCG TAT TAC GAC TTA GTG CCC TCC GAC CCT TCC ATT GAG GAG ATG    1408
Leu Pro Tyr Tyr Asp Leu Val Pro Ser Asp Pro Ser Ile Glu Glu Met
```

-continued

```
                430                 435                 440
CGA AAG GTT GTA TGT GAC CAG AAG CTA CGG CCC AAT GTC CCC AAC TGG      1456
Arg Lys Val Val Cys Asp Gln Lys Leu Arg Pro Asn Val Pro Asn Trp
        445                 450                 455

TGG CAG AGT TAT GAG GCC TTG CGA GTG ATG GGA AAG ATG ATG CGG GAG      1504
Trp Gln Ser Tyr Glu Ala Leu Arg Val Met Gly Lys Met Met Arg Glu
460                 465                 470                 475

TGC TGG TAC GCC AAT GGT GCT GCC CGT CTG ACA GCT CTG CGC ATC AAG      1552
Cys Trp Tyr Ala Asn Gly Ala Ala Arg Leu Thr Ala Leu Arg Ile Lys
                480                 485                 490

AAG ACT CTG TCC CAG CTA AGC GTG CAG GAA GAT GTG AAG ATT              1594
Lys Thr Leu Ser Gln Leu Ser Val Gln Glu Asp Val Lys Ile
        495                 500                 505

TAAGCTGTTA AGATGCCTAC ACAAAGAACC TGGGCAGTGA GGATGACTGC AGG           1647
```

(2) INFORMATION FOR SEQ ID NO: 8:

(i) SEQUENCE CHARACTERISTICS:
        (A) LENGTH: 505 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ala Glu Ser Ala Gly Ala Ser Ser Phe Phe Pro Leu Val Val Leu
 1               5                  10                  15

Leu Leu Ala Gly Ser Gly Gly Ser Gly Pro Arg Gly Ile Gln Ala Leu
                20                  25                  30

Leu Cys Ala Cys Thr Ser Cys Leu Gln Thr Asn Tyr Thr Cys Glu Thr
            35                  40                  45

Asp Gly Ala Cys Met Val Ser Ile Phe Asn Leu Asp Gly Val Glu His
        50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Ile Asp Phe Cys Asn Lys Ile Asp Leu Arg Val Pro Ser Gly His
            100                 105                 110

Leu Lys Glu Pro Ala His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255
```

```
Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
            275                 280                 285

Ser Leu Phe Asp Tyr Leu Asn Arg Tyr Thr Val Thr Ile Glu Gly Met
            290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
            355                 360                 365

Ile Ala Pro Asn Gln Arg Val Gly Thr Lys Arg Tyr Met Ala Pro Glu
            370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415

Cys Asn Ser Gly Gly Val His Glu Asp Tyr Gln Leu Pro Tyr Tyr Asp
            420                 425                 430

Leu Val Pro Ser Asp Pro Ser Ile Glu Glu Met Arg Lys Val Val Cys
            435                 440                 445

Asp Gln Lys Leu Arg Pro Asn Val Pro Asn Trp Trp Gln Ser Tyr Glu
            450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505

(2) INFORMATION FOR SEQ ID NO: 9:

(i) SEQUENCE CHARACTERISTICS:
        (A) LENGTH: 1794 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: W-120

(ix) FEATURE:
        (A) NAME/KEY: CDS
        (B) LOCATION: 83..1591

(xi) SEQUENCE DESCRIPTION: SEQ ID NO: 9:

GAATTCGCGG CCGCGGGCGA GGCTTCCTGA GGAGAAGCTG CGGCCGGGGC CGGGCCGGGC      60

CACAAACAGT GGCGGCGGGA CC ATG GAG GCG GCG GCC GCT GCT CCA CGT CGT     112
                        Met Glu Ala Ala Ala Ala Ala Pro Arg Arg
                         1               5                  10

CCG CAG CTC CTC ATC GTG TTG GTG GCG GCG GCG ACG CTG CTC CCG GGG     160
Pro Gln Leu Leu Ile Val Leu Val Ala Ala Ala Thr Leu Leu Pro Gly
            15                  20                  25
```

```
GCG AAG GCA TTA CAG TGT TTC TGC CAC CTC TGT ACA AAG GAT AAT TTT      208
Ala Lys Ala Leu Gln Cys Phe Cys His Leu Cys Thr Lys Asp Asn Phe
            30                  35                  40

ACC TGT GAG ACA GAT GGT CTT TGC TTT GTC TCA GTC ACT GAG ACC ACA      256
Thr Cys Glu Thr Asp Gly Leu Cys Phe Val Ser Val Thr Glu Thr Thr
            45                  50                  55

GAC AAA GTT ATA CAC AAT AGT ATG TGT ATA GCT GAA ATT GAC CTA ATT      304
Asp Lys Val Ile His Asn Ser Met Cys Ile Ala Glu Ile Asp Leu Ile
        60                  65                  70

CCT CGA GAC AGG CCA TTT GTA TGT GCA CCA TCT TCA AAA ACA GGG GCA      352
Pro Arg Asp Arg Pro Phe Val Cys Ala Pro Ser Ser Lys Thr Gly Ala
75                  80                  85                  90

GTT ACT ACA ACA TAT TGC TGC AAT CAG GAC CAC TGC AAT AAA ATA GAA      400
Val Thr Thr Thr Tyr Cys Cys Asn Gln Asp His Cys Asn Lys Ile Glu
                95                  100                 105

CTC CCA ACT ACA GGA CCT TTT TCA GAA AAG CAG TCA GCT GGC CTT GGT      448
Leu Pro Thr Thr Gly Pro Phe Ser Glu Lys Gln Ser Ala Gly Leu Gly
                110                 115                 120

CCT GTG GAG CTG GCA GCT GTC ATT GCT GGT CCA GTC TGC TTC GTC TGC      496
Pro Val Glu Leu Ala Ala Val Ile Ala Gly Pro Val Cys Phe Val Cys
            125                 130                 135

ATT GCA CTT ATG CTG ATG GTC TAT ATC TGC CAT AAC CGC ACT GTC ATT      544
Ile Ala Leu Met Leu Met Val Tyr Ile Cys His Asn Arg Thr Val Ile
        140                 145                 150

CAC CAC CGT GTG CCA AAT GAA GAG GAT CCA TCA CTA GAT CGC CCT TTC      592
His His Arg Val Pro Asn Glu Glu Asp Pro Ser Leu Asp Arg Pro Phe
155                 160                 165                 170

ATT TCA GAG GGC ACC ACC TTA AAA GAT TTA ATT TAT GAT ATG ACA ACA      640
Ile Ser Glu Gly Thr Thr Leu Lys Asp Leu Ile Tyr Asp Met Thr Thr
                175                 180                 185

TCA GGG TCT GGA TCA GGT TTA CCA CTG CTT GTT CAA AGA ACA ATT GCC      688
Ser Gly Ser Gly Ser Gly Leu Pro Leu Leu Val Gln Arg Thr Ile Ala
                190                 195                 200

AGG ACC ATT GTG TTA CAA GAA AGC ATT GGC AAA GGT CGG TTT GGA GAA      736
Arg Thr Ile Val Leu Gln Glu Ser Ile Gly Lys Gly Arg Phe Gly Glu
            205                 210                 215

GTT TGG CGA GGC AAA TGG CGG GGA GAA GAA GTT GCT GTG AAG ATA TTC      784
Val Trp Arg Gly Lys Trp Arg Gly Glu Glu Val Ala Val Lys Ile Phe
        220                 225                 230

TCT TCT AGA GAA GAG CGT TCA TGG TTC CGA GAG GCA GAG ATT TAT CAG      832
Ser Ser Arg Glu Glu Arg Ser Trp Phe Arg Glu Ala Glu Ile Tyr Gln
235                 240                 245                 250

ACT GTA ATG TTA CGC CAT GAA AAT ATC CTG GGA TTT ATA GCA GCA GAC      880
Thr Val Met Leu Arg His Glu Asn Ile Leu Gly Phe Ile Ala Ala Asp
                255                 260                 265

AAC AAA GAC AAT GGG ACA TGG ACG CAG CTG TGG TTG GTG TCA GAT TAT      928
Asn Lys Asp Asn Gly Thr Trp Thr Gln Leu Trp Leu Val Ser Asp Tyr
                270                 275                 280

CAT GAG CAT GGA TCC CTT TTC GAT TAC TTG AAT AGA TAC ACT GTT ACT      976
His Glu His Gly Ser Leu Phe Asp Tyr Leu Asn Arg Tyr Thr Val Thr
            285                 290                 295

GTG GAA GGA ATG ATC AAG CTT GCT CTG TCC ACA GCA AGT GGT CTT GCC     1024
Val Glu Gly Met Ile Lys Leu Ala Leu Ser Thr Ala Ser Gly Leu Ala
        300                 305                 310

CAT CTT CAC ATG GAG ATT GTT GGT ACC CAA GGA AAA CCA GCT ATT GCC     1072
His Leu His Met Glu Ile Val Gly Thr Gln Gly Lys Pro Ala Ile Ala
315                 320                 325                 330

CAT AGA GAT TTG AAA TCA AAG AAT ATC TTG GTG AAG AAA AAT GGA ACC     1120
His Arg Asp Leu Lys Ser Lys Asn Ile Leu Val Lys Lys Asn Gly Thr
                335                 340                 345
```

```
TGT TGT ATT GCA GAC TTG GGA CTT GCT GTG AGA CAT GAT TCT GCC ACA    1168
Cys Cys Ile Ala Asp Leu Gly Leu Ala Val Arg His Asp Ser Ala Thr
            350                 355                 360

GAT ACA ATT GAT ATT GCT CCA AAC CAC AGA GTA GGC ACT AAA AGG TAC    1216
Asp Thr Ile Asp Ile Ala Pro Asn His Arg Val Gly Thr Lys Arg Tyr
            365                 370                 375

ATG GCC CCT GAA GTT CTA GAT GAT TCC ATA AAT ATG AAA CAT TTT GAA    1264
Met Ala Pro Glu Val Leu Asp Asp Ser Ile Asn Met Lys His Phe Glu
            380                 385                 390

TCC TTC AAA CGC GCT GAC ATC TAT GCA ATG GGC TTA GTG TTC TGG GAA    1312
Ser Phe Lys Arg Ala Asp Ile Tyr Ala Met Gly Leu Val Phe Trp Glu
395                 400                 405                 410

ATT GCT CGA CGC TGT TCT ATT GGT GGA ATC CAT GAA GAC TAT CAG TTG    1360
Ile Ala Arg Arg Cys Ser Ile Gly Gly Ile His Glu Asp Tyr Gln Leu
            415                 420                 425

CCT TAT TAT GAT CTT GTA CCT TCT GAT CCA TCG GTT GAA GAA ATG AGA    1408
Pro Tyr Tyr Asp Leu Val Pro Ser Asp Pro Ser Val Glu Glu Met Arg
            430                 435                 440

AAA GTA GTT TGC GAA CAG AAG TTA AGG CCA AAT ATT CCA AAC AGA TGG    1456
Lys Val Val Cys Glu Gln Lys Leu Arg Pro Asn Ile Pro Asn Arg Trp
            445                 450                 455

CAG AGC TGT GAG GCC TTG AGA GTG ATG GCT AAA ATT ATG AGA GAA TGC    1504
Gln Ser Cys Glu Ala Leu Arg Val Met Ala Lys Ile Met Arg Glu Cys
            460                 465                 470

TGG TAT GCC AAT GGA GCA GCA AGG CTG ACA GCT TTG CGA ATT AAA AAA    1552
Trp Tyr Ala Asn Gly Ala Ala Arg Leu Thr Ala Leu Arg Ile Lys Lys
475                 480                 485                 490

ACA TTG TCA CAA CTC AGC CAA CAG GAA GGC ATC AAA ATG TAACTGAAAC    1601
Thr Leu Ser Gln Leu Ser Gln Gln Glu Gly Ile Lys Met
            495                 500

ACCGTGGGAA CTCTGCTCTC TTCATATCTG CTCCTGGGTG TTTAGGAGGC TGGTTGTTCT    1661

ACCTCACTGA GAGAACAGAG GGCTCTGCTT CCTCTTGCAG CAGTGGAATA TGGTCAACTG    1721

AAAGCTTCCC AGGGTTTCTC TGGGCCCAGA GGCAGCCGTG GGTCCTTCT GTGCACTATG     1781

GATAACTTCT TCC                                                      1794

(2) INFORMATION FOR SEQ ID NO: 10:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO: 10:

Met Gln Ala Ala Ala Ala Pro Arg Arg Pro Gln Leu Leu Ile Val
1               5                   10                  15

Leu Val Ala Ala Ala Thr Leu Leu Pro Gly Ala Lys Ala Leu Gln Cys
                20                  25                  30

Phe Cys His Leu Cys Thr Lys Asp Asn Phe Thr Cys Glu Thr Asp Gly
            35                  40                  45

Leu Cys Phe Val Ser Val Thr Glu Thr Thr Asp Lys Val Ile His Asn
        50                  55                  60

Ser Met Cys Ile Ala Glu Ile Asp Leu Ile Pro Arg Asp Arg Pro Phe
65                  70                  75                  80

Val Cys Ala Pro Ser Ser Lys Thr Gly Ala Val Thr Thr Thr Tyr Cys
                85                  90                  95
```

```
Cys Asn Gln Asp His Cys Asn Lys Ile Glu Leu Pro Thr Thr Gly Pro
                100                 105                 110

Phe Ser Glu Lys Gln Ser Ala Gly Leu Gly Pro Val Glu Leu Ala Ala
            115                 120                 125

Val Ile Ala Gly Pro Val Cys Phe Val Cys Ile Ala Leu Met Leu Met
        130                 135                 140

Val Tyr Ile Cys His Asn Arg Thr Val Ile His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
        210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
        290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
        370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
        450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500
```

(2) INFORMATION FOR SEQ ID NO: 11:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: KDA-B5

(ix) FEATURE:
        (A) NAME/KEY: CDS
        (B) LOCATION: 25..318

(xi) SEQUENCE DESCRIPTION: SEQ ID NO: 11:

```
GGATCCGAAT ACGTGGCGGT TAAA ATA TTC TCC TCC AGG GAT GAG AGA TCT           51
                           Ile Phe Ser Ser Arg Asp Glu Arg Ser
                            1               5

TGG TTC CGT GAG GCG GAA ATT TAT CAG ACG GTG ATG CTG AGA CAC GAG          99
Trp Phe Arg Glu Ala Glu Ile Tyr Gln Thr Val Met Leu Arg His Glu
 10          15                  20                  25

AAC ATC CTC GGT TTC ATC GCA GCT GAC AAC AAA GAT AAT GGA ACT TGG         147
Asn Ile Leu Gly Phe Ile Ala Ala Asp Asn Lys Asp Asn Gly Thr Trp
             30                  35                  40

ACA CAA CTC TGG CTT GTG TCA GAG TAT CAC GAG CAG GGC TCC TTG TAT         195
Thr Gln Leu Trp Leu Val Ser Glu Tyr His Glu Gln Gly Ser Leu Tyr
                 45                  50                  55

GAC TAT TTG AAC AGA AAC ATA GTG ACT GTG GCT GGA ATG GTC AAG CTG         243
Asp Tyr Leu Asn Arg Asn Ile Val Thr Val Ala Gly Met Val Lys Leu
             60                  65                  70

GCG CTT TCC ATA GCG AGT GGT CTG GCT CAC CTG CAC ATG GAG ATC GTG         291
Ala Leu Ser Ile Ala Ser Gly Leu Ala His Leu His Met Glu Ile Val
 75                  80                  85

GGT ACT CAA GGT AAG CTT GCT ATT GCT CACGGTGATA TCAAAAGTCT               338
Gly Thr Gln Gly Lys Leu Ala Ile Ala
 90                  95

AGA                                                                     341
```

(2) INFORMATION FOR SEQ ID NO: 12:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO: 12:

```
Ile Phe Ser Ser Arg Asp Glu Arg Ser Trp Phe Arg Glu Ala Glu Ile
 1               5                  10                  15

Tyr Gln Thr Val Met Leu Arg His Glu Asn Ile Leu Gly Phe Ile Ala
             20                  25                  30

Ala Asp Asn Lys Asp Asn Gly Thr Trp Thr Gln Leu Trp Leu Val Ser
         35                  40                  45

Glu Tyr His Glu Gln Gly Ser Leu Tyr Asp Tyr Leu Asn Arg Asn Ile
     50                  55                  60

Val Thr Val Ala Gly Met Val Lys Leu Ala Leu Ser Ile Ala Ser Gly
 65                  70                  75                  80

Leu Ala His Leu His Met Glu Ile Val Gly Thr Gln Gly Lys Leu Ala
                 85                  90                  95
```

Ile Ala (2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PRIMER A (xi) SEQUENCE DESCRIPTION: SEQ ID NO: 13:

GCGGATCCGA RTAYGTNGCN GTNAAR                                    26

(2) INFORMATION FOR SEQ ID NO: 14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (A) LIBRARY: PRIMER B (xi) SEQUENCE DESCRIPTION: SEQ ID NO: 14:

GACTGTAGAR CTYTTDATRT CYCTRTG                                   27

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PRIMER C (xi) SEQUENCE DESCRIPTION: SEQ ID NO: 15:

GACTCTAGAR CTYTTDATRT CNCGRTG                                   27

(2) INFORMATION FOR SEQ ID NO: 16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PRIMER D (xi) SEQUENCE DESCRIPTION: SEQ ID NO: 16:

GACTCTAGNG AYTTDATRTC YCTRTG                                    26

(2) INFORMATION FOR SEQ ID NO: 17:

(i) SEQUENCE CHARACTERISTICS:
        (A) LENGTH: 27 base pairs

```
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: PRIMER E (xi) SEQUENCE DESCRIPTION: SEQ ID NO: 17:

GACTCTAGAN GAYTTDATRT CNCGRTG                                   27

(2) INFORMATION FOR SEQ ID NO: 18:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: PEPTIDE SEQUENCE OF KDA-B5 USED TO DESIGN
             PRIMER A (xi) SEQUENCE DESCRIPTION: SEQ ID NO: 18:

Asn Glu Tyr Val Ala Val Lys
1               5

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: PEPTIDE SEQUENCE OF KDA-B5 USED TO DESIGN
             PRIMERS B THRU E (xi) SEQUENCE DESCRIPTION: SEQ ID NO: 19:

His Arg Asp Ile Lys Ser
1               5
```